(12) United States Patent
Knuebel et al.

(10) Patent No.: US 7,081,140 B2
(45) Date of Patent: Jul. 25, 2006

(54) DEVELOPER COMPONENTS AND THEIR USE FOR DYEING KERATINIC FIBERS

(75) Inventors: Georg Knuebel, Duesseldorf (DE); Horst Hoeffkes, Duesseldorf (DE); Bernd Meinigke, Leverkusen (DE); Helmut Giesa, Meerbusch (DE)

(73) Assignee: Henkel Kommanditgesellschaft Auf Aktien (Henkel KGAA), Duesseldorf (DE)

( * ) Notice: Subject to any disclaimer, the term of this patent is extended or adjusted under 35 U.S.C. 154(b) by 35 days.

(21) Appl. No.: 10/831,705

(22) Filed: Apr. 23, 2004

(65) Prior Publication Data

US 2004/0255402 A1  Dec. 23, 2004

Related U.S. Application Data

(63) Continuation of application No. PCT/EP02/11622, filed on Oct. 17, 2002.

(30) Foreign Application Priority Data

Oct. 26, 2001  (DE) ................. 101 52 941

(51) Int. Cl.
*A61K 7/13* (2006.01)
(52) U.S. Cl. .................. 8/405; 8/406; 8/421; 8/570; 8/573; 548/400
(58) Field of Classification Search .................. 8/405, 8/406, 410, 421, 570, 573; 548/400
See application file for complete search history.

(56) References Cited

U.S. PATENT DOCUMENTS

| RE30,199 E | 1/1980 | Rose et al. ............... 8/409 |
| 4,865,774 A | 9/1989 | Fabry et al. ............. 252/554 |
| 4,931,218 A | 6/1990 | Schenker et al. ......... 252/991 |
| 5,061,289 A | 10/1991 | Clausen et al. ........... 8/409 |
| 5,294,726 A | 3/1994 | Behler et al. ............. 594/98 |
| 5,380,340 A | 1/1995 | Neunhoeffer et al. ..... 8/409 |
| 5,534,267 A | 7/1996 | Neunhoeffer et al. ..... 424/70.1 |
| 5,663,366 A | 9/1997 | Neunhoeffer et al. ..... 548/371.4 |
| 5,766,576 A | 6/1998 | Lowe et al. ............... 424/407 |
| 6,099,592 A | 8/2000 | Vidal et al. ............... 8/409 |
| 6,284,003 B1 | 9/2001 | Rose et al. ............... 8/412 |
| 6,340,371 B1 | 1/2002 | Genet et al. .............. 8/406 |
| 6,436,152 B1 | 8/2002 | Chassot et al. ........... 8/409 |
| 6,638,321 B1 | 10/2003 | Genet et al. .............. 8/407 |
| 2003/0070240 A1* | 4/2003 | Chassot et al. ........... 8/405 |

FOREIGN PATENT DOCUMENTS

| DE | 23 59 399 A1 | 6/1975 |
| DE | 37 23 354 A1 | 1/1989 |
| DE | 37 25 030 A1 | 2/1989 |
| DE | 38 43 892 A1 | 6/1990 |
| DE | 39 26 344 A1 | 2/1991 |
| DE | 41 33 957 A1 | 4/1993 |
| DE | 195 43 988 A1 | 5/1997 |
| EP | 0 740 931 B1 | 8/1997 |
| EP | 0 984 007 A1 | 3/2000 |
| EP | 1 116 711 A2 | 7/2001 |
| GB | 1 026 978 | 4/1966 |
| GB | 1 153 196 | 5/1969 |
| JP | 02-19576 | 1/1990 |
| WO | WO 94/08969 A1 | 4/1994 |
| WO | WO 94/08970 A1 | 4/1994 |
| WO | WO 96/15765 A1 | 5/1996 |
| WO | WO 99/03836 A1 | 1/1999 |

OTHER PUBLICATIONS

Ch. Zviak, The Science of Hair Care, Chapter 7, pp. 248-250, vol. 7, Dermatology, Verlag Marcel Dekker Inc., New York, Basel (1986).
Ch. Zviak, The Science of Hair Care, Chapter 8, pp. 264-267, vol. 7, Dermatology, Verlag Marcel Dekker Inc., New York, Basel (1986).
European Inventory of Cosmetic Ingredients, Colipa, Mar. 1996, on diskette
Schrader, Grundlagen und Resepturen der Kosmetika, 2nd Edition, Huthig, Buch Verlag, Heidelberg, (1989).
Taschanlexkion der Farben, A. Kornerup u. J H. Wanscher, 3. unveranderte Auflage, 1981.

* cited by examiner

Primary Examiner—Eisa Elhilo
(74) Attorney, Agent, or Firm—Woodcock Washburn LLP

(57) ABSTRACT

Compositions for dyeing keratinic fibers, which contain p-phenylene-diamine derivative substituted by an imidazolyl group, the use of these compounds for dyeing keratinic fibers and a process for dyeing keratinic fibers using these compounds.

21 Claims, No Drawings

DEVELOPER COMPONENTS AND THEIR USE FOR DYEING KERATINIC FIBERS

CROSS REFERENCE TO RELATED APPLICATIONS

This application is a continuation under 35 U.S.C. § 365(c) and 35 U.S.C. § 120 of international application PCT/EP02/11622, filed Oct. 17, 2002. This application also claims priority under 35 U.S.C. § 119 of DE101 52 941.4, filed Oct. 26, 2001, which is incorporated herein by reference in its entirety.

BACKGROUND OF THE INVENTION

The present invention relates to compositions for dyeing keratinic fibers, which contain p-phenylene-diamine derivative substituted by an imidazolyl group, the use of these compounds for dyeing keratinic fibers, a process for dyeing fibers using these compounds, and some of these p-phenylenediamine derivatives per se.

For dyeing keratinic fibers, in particular human hair, "oxidation dyes", because of their intense color and good fastness properties, play a preferred role. Such colorants contain oxidation dye precursors, "developer components" and "coupler components". Under the influence of oxidants or of atmospheric oxygen, the developer components form the actual dyes mutually or by coupling with one or more coupler components.

The developer components employed are customarily primary aromatic amines having a further free or substituted hydroxy or amino group situated in the para- or ortho-position, diaminopyridine derivatives, heterocyclic hydrazones, 4-aminopyrazolone derivatives and 2,4,5,6-tetraaminopyrimidine and its derivatives.

Specific representatives are, for example, p-phenylenediamine, p-toluylenediamine, 2,4,5,6-tetraamino-pyrimidine, p-aminophenol, N,N-bis(2'-hydroxyethyl)-p-phenylenediamine, 2-(2',5'-diaminophenyl)ethanol, 2-(2',5'-diaminophenoxy)ethanol, 1-phenyl-3-carboxy-amido-4-aminopyrazol-5-one, 4-amino-3-methylphenol, 2-aminomethyl-4-aminophenol, 2-hydroxy-4,5,6-triaminopyrimidine, 2,4-dihydroxy-5,6-diaminopyrimidine, 2,5,6-triamino-4-hydroxypyrimidine and 1,3-N,N'-bis(2'-hydroxyethyl)-N,N'-bis(4'-aminophenyl)diaminopropan-2-ol.

The coupler components used are, as a rule, m-phenylenediamine derivatives, naphthols, resorcinol and resorcinol derivatives, pyrazolones and m-amino-phenols. Suitable coupler substances are, in particular, 1-naphthol, 1,5-, 2,7- and 1,7-dihydroxy-naphthalene, 5-amino-2-methylphenol, m-aminophenol, resorcinol, resorcinol monomethyl ether, m-phenylene-diamine, 1-phenyl-3-methylpyrazol-5-one, 2,4-dichloro-3-aminophenol, 1,3-bis(2,4-diaminophenoxy) propane, 2-chlororesorcinol, 4-chlororesorcinol, 2-chloro-6-methyl-3-aminophenol, 2-methylresorcinol, 5-methyl-resorcinol and 2-methyl-4-chloro-5-aminophenol.

Good oxidation dye precursors should primarily fulfill the following requirements: they must form the desired color shades in adequate intensity and fastness on oxidative coupling. They must further possess a good absorptive power to the fibers, where in particular in the case of human hair no noticeable differences must exist between damaged hair and freshly rewashed hair (leveling power). They should be resistant to light, heat, perspiration, friction and the influence of chemical reductants, e.g. permanent waving liquids. Finally, they should—if being used as hair dyes—not dye the scalp too much, and, especially, they should be harmless toxicologically and dermatologically. Furthermore, the dyeing obtained should be able to be removed easily from the hair again by bleaching if it does not conform to the individual wishes of the particular person and is to be reversed.

Using a developer component or a specific coupler/developer combination on its own, as a rule it is not possible to obtain a color shade acting naturally on the hair. In practice, combinations of various developer and/or coupler components are therefore customarily employed. There is therefore continually a need for novel, improved dye components, which are also nonproblematical toxicologically and dermatologically.

It was therefore an object of the present invention to develop novel developer components which fulfill the requirements placed on oxidation dye precursors and make possible dyeings in a wide color spectrum having good fastness properties.

Surprisingly, it has now been found that specific imidazole-substituted p-phenylenediamine derivatives meet the requirements placed on oxidation dye precursors to a high extent. The developer components according to the invention are distinguished by intense color results with excellent perspiration fastness and cold wave fastness. The color loss of dyeings in combination with conventional dye precursors is shifted somewhat to bluish compared with the dyeings using p-toluylenediamine.

DESCRIPTION OF THE INVENTION

The present invention therefore relates firstly to compositions for dyeing keratinic fibers, in particular human hair, which contain, in a cosmetically acceptable carrier, at least one p-phenylenediamine derivative of the formula (I)

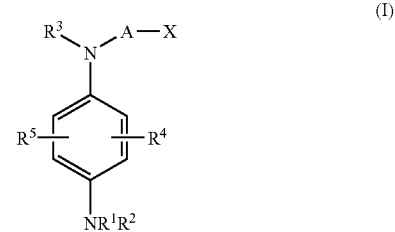

where
A is a branched or unbranched alkylene group having 1 to 6 carbon atoms, which can optionally carry one or more substituents, selected from hydroxy group(s) and halogen atom(s),
X is an optionally substituted imidazolyl radical,
$R^1$, $R^2$ and $R^3$ are, independently of one another, a hydrogen atom, a $C_1$- to $C_4$-alkyl group, a $C_1$- to $C_4$-monohydroxyalkyl group or a $C_2$- to $C_6$-polyhydroxyalkyl group, and
$R^4$ and $R^5$ are, independently of one another, a hydrogen atom, a $C_1$- to $C_4$-alkyl group, a $C_1$- to $C_4$-alkoxy group, a $C_1$- to $C_4$-monohydroxyalkyl group, a $C_2$- to $C_4$-polyhydroxyalkyl group or a halogen atom.

Keratin fibers are in this case understood according to the invention as meaning pelts, wool, feathers and in particular human hair. Although the oxidation dyes according to the invention are primarily suitable for dyeing keratin fibers, in principle nothing stands in the way of use in other fields too, in particular in color photography.

Since the dye precursors according to the invention are amino compounds, the known acid addition salts can be prepared from these in the customary manner. All statements of this specification and accordingly of the claimed scope of protection therefore relate both to the compounds present in free form and to their water-soluble, physiologically tolerable salts. Examples of such salts are the hydrochlorides, the hydrobromides, the sulfates, the phosphates, the acetates, the propionates, the citrates and the lactates. The hydrochlorides and the sulfates are in this case particularly preferred.

Examples of the $C_1$- to $C_4$-alkyl groups mentioned as substituents in the compounds according to the invention are the groups methyl, ethyl, propyl, isopropyl and butyl. Ethyl and methyl are preferred alkyl radicals. Preferred $C_1$- to $C_4$-alkoxy groups are the groups methoxy and ethoxy. Furthermore, it is possible to mention as preferred examples of a $C_1$- to $C_4$-monohydroxyalkyl group a hydroxymethyl, a 2-hydroxy-ethyl, a 3-hydroxypropyl or a 4-hydroxybutyl group. A 2-hydroxyethyl group is particularly preferred. A particularly preferred $C_2$- to $C_4$-polyhydroxyalkyl group is the 1,2-dihydroxyethyl group. Examples of halogen atoms are, according to the invention, F, Cl or Br atoms, Cl atoms are very particularly preferred.

Preferred compounds of the formula (I) are those in which $R^1$, $R^2$ and $R^3$ are a hydrogen atom. The compounds are furthermore preferred in which $R^4$ and $R^5$ are, independently of one another, a hydrogen atom, a methyl group, a chlorine or a fluorine atom. Compounds of the formula (I) in which $R^4$ and $R^5$ are a hydrogen atom are particularly preferred.

An important feature of the compounds of the formula (I) according to the invention is the optionally substituted imidazolyl radical. In a first preferred embodiment of the present invention, the group X is an optionally substituted imidazolyl radical of the formula (II)

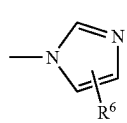
(II)

where $R^6$ is a hydrogen atom, a $C_1$- to $C_4$-alkyl group, a $C_1$- to $C_4$-monohydroxyalkyl group, a $C_2$- to $C_4$-polyhydroxyalkyl group or a halogen atom.

In the context of this embodiment, compounds of the formula (I) are particularly preferred in which A is an unbranched alkylene group having 2 to 6 carbon atoms. A particularly preferred alkylene group in the context of this embodiment is the trimethylene group.

Very particularly preferred compound of the formula (I) having an imidazolyl radical of the formula (II) are (4-amino-phenyl)(3-(imidazol-1-yl)propyl)amine (E2) of the formula (IIa)

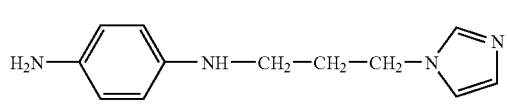
(IIa)

and (4-amino-3-methylphenyl)(3-(imidazol-1-yl)propyl) amine (E3) of the formula (IIb)

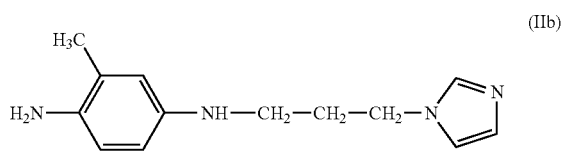
(IIb)

In the context of a second preferred embodiment of the present invention, the optionally substituted imid-azolyl radical X is and a group of the formula (III)

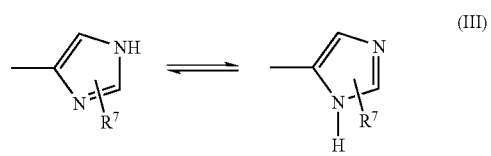
(III)

where $R^7$ is a hydrogen atom, a $C_1$- to $C_4$-alkyl group, a $C_1$- to $C_4$-monohydroxyalkyl group, a $C_2$- to $C_4$-polyhydroxyalkyl group or a halogen atom. Since the compounds of this embodiment of the present invention are present in the form of a tautomeric equilibrium, the statements of this specification relate to both tautomers present in the equilibrium.

In the context of this embodiment of the present invention, the group A is preferably an unbranched alkylene group having 1 to 6 carbon atoms. Particularly preferred manner, the group A is an ethylene group.

A very particularly preferred compound of the formula (I) having an imidazolyl radical of the formula (III) is (4-aminophenyl)(2-(imidazol-5-yl)ethyl)amine (E1) of the formula (IIIa)

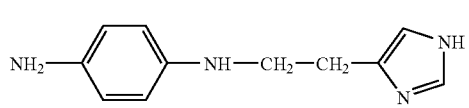
(IIIa)

In addition to the compounds of the formula (I) according to the invention, the colorants can contain one or more further dye precursors.

The present invention is subject to no restrictions at all with respect to the further dye precursors which can be employed in the colorants according to the invention. The colorants according to the invention can contain, as further dye precursors oxidation dye precursors of the developer and/or coupler type, and precursors of naturally analogous dyes, such as indole and indoline derivatives, and mixtures of representatives of these groups.

In a first preferred embodiment, the colorant contains at least one further developer component. The developer components employed are customarily primary aromatic amines having a further free or substituted hydroxy or amino group situated in the para- or ortho-position, diaminopyridine derivatives, heterocyclic hydrazones, 4-aminopyrazole derivatives and 2,4,5,6-tetraamino-pyrimidine and its derivatives.

It can be preferred according to the invention to employ as the developer component a p-phenylenediamine derivative or one of its physiologically tolerable salts. Those particularly preferred are p-phenylene-diamine derivatives of the formula (E1)

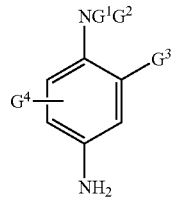

where
$G^1$ is a hydrogen atom, a $C_1$- to $C_4$-alkyl radical, a $C_1$- to $C_4$-monohydroxyalkyl radical, a $C_2$- to $C_4$-polyhydroxyalkyl radical, a $(C_1$- to $C_4)$-alkoxy-$(C_1$- to $C_4)$-alkyl radical, a 4'-aminophenyl radical or a $C_1$- to $C_4$-alkyl radical, which is substituted by a nitrogen-containing group, a phenyl or a 4'-aminophenyl radical;

$G^2$ is a hydrogen atom, a $C_1$- to $C_4$-alkyl radical, a $C_1$- to $C_4$-monohydroxyalkyl radical, a $C_2$- to $C_4$-polyhydroxyalkyl radical, a $(C_1$ to $C_4)$-alkoxy-$(C_1$- to $C_4)$-alkyl radical or a $C_1$- to $C_4$-alkyl radical which is substituted by a nitrogen-containing group;

$G^3$ is a hydrogen atom, a halogen atom, such as a chlorine, bromine, iodine or fluorine atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-hydroxy-alkoxy radical, a $C_1$- to $C_4$-acetylaminoalkoxy radical, a $C_1$- to $C_4$-mesylaminoalkoxy radical or a $C_1$- to $C_4$-carbamoylaminoalkoxy radical;

$G^4$ is a hydrogen atom, a halogen atom or a $C_1$- to $C_4$-alkyl radical or if $G^3$ and $G^4$ are in the ortho-position to one another, they can together form a bridging $\alpha,\omega$-alkylenedioxo group, such as, for example, an ethylenedioxy group.

Examples of the $C_1$- to $C_4$-alkyl radicals mentioned as substituents in the compounds according to the invention are the groups methyl, ethyl, propyl, isopropyl and butyl. Ethyl and methyl are preferred alkyl radicals. Preferred $C_1$- to $C_4$-alkoxy radicals of the invention are, for example, a methoxy or an ethoxy group. Preferred examples of a $C_1$- to $C_4$-hydroxyalkyl group which can furthermore be mentioned are a hydroxymethyl, a 2-hydroxyethyl, a 3-hydroxypropyl or a 4-hydroxybutyl group; a 2-hydroxyethyl group is particularly preferred. A particularly preferred $C_2$- to $C_4$-polyhydroxyalkyl group is the 1,2-dihydroxyethyl group. Examples of halogen atoms are F, Cl or Br atoms according to the invention; Cl atoms are very particularly preferred. The further terms used are derived according to the invention from the definitions given here. Examples of nitrogen-containing groups of the formula (E1) are in particular the amino groups, $C_1$- to $C_4$-monoalkylamino groups, $C_1$- to $C_4$-dialkylamino groups, $C_1$- to $C_4$-trialkylammonium groups, $C_1$- to $C_4$-monohydroxyalkylamino groups, imidazolinium and ammonium.

Particularly preferred p-phenylenediamines of the formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis($\beta$-hydroxyethyl)-p-phenylenediamine, 4-N,N-bis($\beta$-hydroxyethyl)amino-2-methylaniline, 4-N,N-bis($\beta$-hydroxyethyl)amino-2-chloroaniline, 2-($\beta$-hydroxy-ethyl)-p-phenylenediamine, 2-($\alpha,\beta$-dihydroxyethyl)-p-phenylenediamine, 2-fluoro-p-phenylenediamine, 2-isopropyl-p-phenylenediamine, N-($\beta$-hydroxypropyl)-p-phenylenediamine, 2-hydroxymethyl-p-phenylenediamine, N,N-dimethyl-3-methyl-p-phenylenediamine, N,N-(ethyl, $\beta$-hydroxyethyl)-p-phenylenediamine, N-($\beta,\gamma$-dihydroxypropyl)-p-phenylenediamine, N-(4'-aminophenyl)-p-phenylenediamine, N-phenyl-p-phenylenediamine, 2-($\beta$-hydroxyethyloxy)-p-phenylenediamine, 2-($\beta$-acetylaminoethyloxy)-p-phenylenediamine, N-($\beta$-methoxyethyl)-p-phenylenediamine and 5,8-diaminobenzo-1,4-dioxane, and their physiologically tolerable salts.

According to the invention, very particularly preferred p-phenylenediamine derivatives of the formula (E1) are p-phenylenediamine, p-toluylenediamine, 2-($\beta$-hydroxyethyl)-p-phenylenediamine, 2-($\alpha,\beta$-dihydroxyethyl)-p-phenylenediamine and N,N-bis($\beta$-hydroxyethyl)-p-phenylenediamine.

It can furthermore be preferred according to the invention to employ as the developer component compounds which contain at least two aromatic nuclei which are substituted by amino and/or hydroxyl groups.

Among the binuclear developer components which can be used in the dyeing compositions according to the invention, it is possible in particular to mention the compounds which correspond to the following formula (E2), and their physiologically tolerable salts:

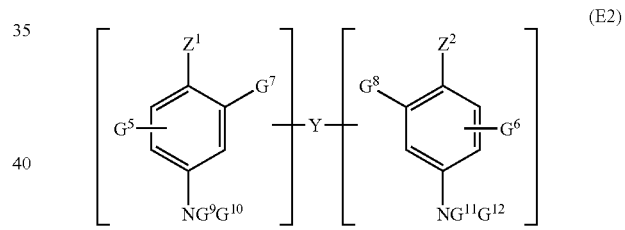

where:
$Z^1$ and $Z^2$ are, independently of one another, a hydroxyl or $NH_2$ radical, which is optionally substituted by a $C_1$- to $C_4$-alkyl radical, by a $C_1$- to $C_4$-hydroxyalkyl radical and/or by a bridging Y or which is optionally part of a bridging ring system, the bridging Y is an alkylene group having 1 to 14 carbon atoms, such as, for example, a linear or branched alkylene chain or an alkylene ring, which can be interrupted or terminated by one or more nitrogen-containing groups and/or one or more heteroatoms such as oxygen, sulfur or nitrogen atoms and can possibly be substituted by one or more hydroxyl or $C_1$- to $C_8$-alkoxy radicals, or a direct bond, $G^5$ and $G^6$ are, independently of one another, a hydrogen or halogen atom, a $C_1$- to $C_4$-alkyl radical, a $C_1$- to $C_4$-monohydroxyalkyl radical a $C_2$- to $C_4$-polyhydroxyalkyl radical, a $C_1$- to $C_4$-aminoalkyl radical or a direct link to the bridging Y, $G^7$, $G^8$, $G^9$, $G^{10}$, $G^{11}$ and $G^{12}$ are, independently of one another, a hydrogen atom, a direct bond to the bridging Y or a $C_1$- to $C_4$-alkyl radical, with the provisos that the compounds of the formula (E2) contain only one bridging Y per molecule and the compounds of the formula (E2) contain at least one amino group which carries at least one hydrogen atom.

The substituents used in formula (E2) are, according to the invention, defined analogously to the above embodiments.

Preferred binuclear developer components of the formula (E2) are in particular:

N,N'-bis(β-hydroxyethyl)-N,N'-bis(4'-aminophenyl)-1,3-diaminopropan-2-ol, N,N-bis(β-hydroxyethyl)-N,N'-bis(4'-aminophenyl)ethylenediamine, N,N'-bis(4-amino-phenyl)tetramethylenediamine, N,N'-bis(β-hydroxyethyl)-N,N'-bis(4-minophenyl)tetramethylenediamine, N,N'-bis-(4-methylaminophenyl)tetramethylenediamine, N,N'-di-ethyl-N,N'-bis(4'-amino-3'-methylphenyl)ethylene-diamine, bis(2-hydroxy-5-aminophenyl)methane, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically tolerable salts.

Very particularly preferred binuclear developer components of the formula (E2) are N,N'-bis(β-hydroxyethyl)-N,N'-bis(4'-aminophenyl)-1,3-diamino-propan-2-ol, bis(2-hydroxy-5-aminophenyl)methane, N,N'-bis(4'-aminophenyl)-1,4-diazacycloheptane and 1,10-bis(2',5'-diaminophenyl)-1,4,7,10-tetraoxadecane or one of their physiologically tolerable salts.

It can furthermore be preferred according to the invention to employ as the developer component a p-aminophenol derivative or one of its physiologically tolerable salts. Those particularly preferred are p-aminophenol derivatives of the formula (E3)

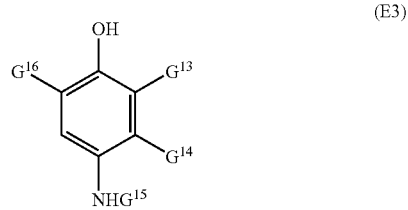

(E3)

where:

$G^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$ to $C_4$)-alkoxy-($C_1$- to $C_4$)-alkyl radical, a $C_1$- to $C_4$-aminoalkyl radical, a hydroxy-($C_1$ to $C_4$)-alkylamino radical, a $C_1$- to $C_4$-hydroxyalkoxy radical, a $C_1$- to $C_4$-hydroxyalkyl-($C_1$- to $C_4$)-aminoalkyl radical or a (di-$C_1$- to $C_4$-alkylamino)-($C_1$- to $C_4$)-alkyl radical, and $G^{14}$ is a hydrogen or halogen atom, a $C_1$- to $C_4$-alkyl radical, a $C_1$- to $C_4$-monohydroxyalkyl radical, a $C_2$ to $C_4$-polyhydroxyalkyl radical, a ($C_1$- to $C_4$)-alkoxy-($C_1$ to $C_4$)-alkyl radical, a $C_1$- to $C_4$-aminoalkyl radical or a $C_1$- to $C_4$-cyanoalkyl radical, $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and $G^{16}$ is hydrogen or a halogen atom.

The substituents used in formula (E3) are, according to the invention, defined analogously to the above embodiments.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethyl-phenol, 4-amino-2-(β-hydroxyethylaminomethyl)phenol, 4-amino-2-(α,β-dihydroxyethyl)phenol, 4-amino-2-fluoro-phenol, 4-amino-2-chlorophenol, 4-amino-2,6-dichloro-phenol, 4-amino-2-(diethylaminomethyl)phenol, and their physiologically tolerable salts.

Very particularly preferred compounds of the formula (E3) are p-aminophenol, 4-amino-3-methylphenol, 4-amino-2-aminomethylphenol, 4-amino-2-(a,β-dihydroxyethyl)phenol and 4-amino-2-(diethylaminomethyl)phenol.

The developer component can further be selected from o-aminophenol and its derivatives, such as, for example, 2-amino-4-methylphenol, 2-amino-5-methylphenol or 2-amino-4-chlorophenol.

The developer component can furthermore be selected from heterocyclic developer components, such as, for example, the pyridine, pyrimidine, pyrazole, pyrazolo-pyrimidine derivatives and their physiologically tolerable salts.

Preferred pyridine derivatives are in particular the compounds which are described in the patents GB 1 026 978 and GB 1 153 196, such as 2,5-diaminopyridine, 2-(4'-methoxyphenyl)amino-3-amino-pyridine, 2,3-diamino-6-methoxypyridine, 2-(β-methoxy-ethyl)amino-3-amino-6-methoxypyridine and 3,4-diamino-pyridine.

Preferred pyrimidine derivatives are in particular the compounds which are described in German Patent DE 2 359 399, Japanese laid-open application JP 02019576 A2 or in laid-open application WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-di-hydroxy-5,6-diaminopyrimidine and 2,5,6-triamino-pyrimidine.

Preferred pyrazole derivatives are in particular the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-di-amino-1-(4'-chlorobenzyl)pyrazole, 4,5-diamino-1,3-di-methylpyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methylpyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-iso-propylpyrazole, 4,5-diamino-3-methyl-1-isopropyl-pyrazole, 4-amino-5-(β-aminoethyl)amino-1,3-dimethyl-pyrazole, 3,4,5-triaminopyrazole, 1-methyl-3,4,5-tri-aminopyrazole, 3,5-diamino-1-methyl-4-methylamino-pyrazole and 3,5-diamino-4-(β-hydroxyethyl)amino-1-methylpyrazole.

Preferred pyrazolopyrimidine derivatives are in particular the derivatives of pyrazolo-[1,5-a]-pyrimidine of the following formula (E4) and its tautomeric forms, if a tautomeric equilibrium exists:

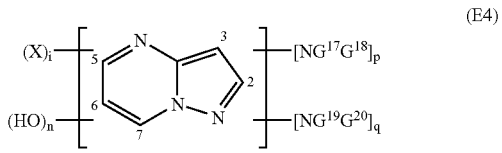

(E4)

where:
- $G^{17}$, $G^{18}$, $G^{19}$ and $G^{20}$ are, independently of one another, a hydrogen atom, a $C_1$- to $C_4$-alkyl radical, an aryl radical, a $C_1$- to $C_4$-hydroxyalkyl radical, a $C_2$ to $C_4$-polyhydroxyalkyl radical, a $(C_1$- to $C_4)$-alkoxy-$(C_1$- to $C_4)$-alkyl radical, a $C_1$ to $C_4$-aminoalkyl radical which can optionally be protected by an acetylureido or a sulfonyl radical, a $(C_1$- to $C_4)$-alkylamino-$(C_1$- to $C_4)$-alkyl radical, a di-$[(C_1$- to $C_4)$-alkyl]-$(C_1$ to $C_4)$-aminoalkyl radical, where the dialkyl radicals optionally form a carbon cycle or a heterocycle having 5 or 6 chain members, a $C_1$- to $C_4$-hydroxyalkyl or a di-$(C_1$- to $C_4)$-[hydroxyalkyl]-$(C_1$- to $C_4)$-aminoalkyl radical,
- the X radicals are independently of one another a hydrogen atom, a $C_1$- to $C_4$-alkyl radical, an aryl radical, a $C_1$- to $C_4$-hydroxyalkyl radical, a $C_2$- to $C_4$-polyhydroxyalkyl radical, a $C_1$- to $C_4$-aminoalkyl radical, a $(C_1$- to $C_4)$-alkylamino-$(C_1$- to $C_4)$-alkyl radical, a di-$[(C_1$- to $C_4)$alkyl]-$(C_1$- to $C_4)$-aminoalkyl radical, where the dialkyl radicals optionally form a carbon cycle or a heterocycle having 5 or 6 chain members, a $C_1$- to $C_4$-hydroxyalkyl- or a di-$(C_1$- to $C_4$-hydroxyalkyl)aminoalkyl radical, an amino radical, a $C_1$- to $C_4$-alkyl- or di-$(C_1$- to $C_4$-hydroxyalkyl)amino radical, a halogen atom, a carboxylic acid group or a sulfonic acid group,
- i has the value 0, 1, 2 or 3,
- p has the value 0 or 1,
- q has the value 0 or 1 and
- n has the value 0 or 1, with the proviso that
the sum of p+q is not equal to 0,
if p+q is equal to 2, n has the value 0, and the groups $NG^{17}G^{18}$ and $NG^{19}G^{20}$ occupy the positions (2,3); (5,6); (6,7); (3,5) or (3,7);
if p+q is equal to 1, n has the value 1, and the groups $NG^{17}G^{18}$ (or $NG^{19}G^{20}$) and the group OH occupy the positions (2,3); (5,6); (6,7); (3,5) or (3,7);

The substituents used in formula (E4) are defined, according to the invention, analogously to the above embodiments.

If the pyrazolo-[1,5-a]-pyrimidine of the above-mentioned formula (E4) contains a hydroxy group in one of the positions 2, 5 or 7 of the ring system, a tautomeric equilibrium exists, which is shown, for example, in the following scheme:

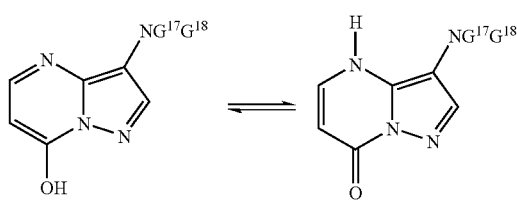

Among the pyrazolo-[1,5-a]-pyrimidines of the abovementioned formula (E4), the following can in particular be mentioned:
pyrazolo-[1,5-a]-pyrimidine-3,7-diamine;
2,5-dimethylpyrazolo-[1,5-a]-pyrimidine-3,7-di-amine;
pyrazolo-[1,5-a]-pyrimidine-3,5-diamine;
2,7-dimethylpyrazolo-[1,5-a]-pyrimidine-3,5-di-amine;
3-aminopyrazolo-[1,5-a]-pyrimidin-7-ol;
3-aminopyrazolo-[1,5-a]-pyrimidin-5-ol;
2-(3-aminopyrazolo-[1,5-a]-pyrimidin-7-ylamino)-ethanol;
2-(7-aminopyrazolo-[1,5-a]-pyrimidin-3-ylamino)-ethanol;
2-[(3-aminopyrazolo-[1,5-a]-pyrimidin-7-yl)-(2-hydroxyethyl)amino]ethanol;
2-[(7-aminopyrazolo-[1,5-a]-pyrimidin-3-yl)-(2-hydroxyethyl)amino]ethanol;
5,6-dimethylpyrazolo-[1,5-a]-pyrimidine-3,7-di-amine;
2,6-dimethylpyrazolo-[1,5-a]-pyrimidine-3,7-di-amine;
3-amino-7-dimethylamino-2,5-dimethylpyrazole-[1,5-a]-pyrimidine, and their physiologically tolerable salts and their tautomeric forms if a tautomeric equilibrium is present.

The pyrazolo-[1,5-a]-pyrimidines of the abovementioned formula (E4) can be prepared as described in the literature by cyclization starting from an amino-pyrazole or from hydrazine.

In a second preferred embodiment, the colorants according to the invention contain at least one coupler component.

The coupler components used are as a rule m-phenylenediamine derivatives, naphthols, resorcinol and resorcinol derivatives, pyrazolones and m-aminophenol derivatives. Suitable coupler substances are in particular 1-naphthol, 1,5-, 2,7- and 1,7-dihydroxynaphthalene, 5-amino-2-methylphenol, m-amino-phenol, resorcinol, resorcinol monomethyl ether, m-phenylenediamine, 1-phenyl-3-methylpyrazol-5-one, 2,4-dichloro-3-aminophenol, 1,3-bis(2',4'-diamino-phenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Preferred coupler components according to the invention are
m-aminophenol and its derivatives such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxy-ethyl)amino-2-methylphenol, 3-(diethylamino)-phenol, N-cyclopentyl-3-aminophenol, 1,3-di-hydroxy-5-(methylamino)benzene, 3-ethylamino-4-methylphenol and 2,4-dichloro-3-aminophenol,
o-aminophenol and its derivatives,
m-diaminobenzene and its derivatives such as, for example, 2,4-diaminophenoxyethanol, 1,3-bis-(2',4'-diaminophenoxy)propane, 1-methoxy-2-amino-4-(2'-hydroxyethylamino)benzene, 1,3-bis(2',4'-di-aminophenyl)propane, 2,6-bis(2'-hydroxyethyl-amino)-1-methylbenzene and 1-amino-3-bis(2'-hydroxyethyl)aminobenzene,
o-diaminobenzene and its derivatives such as, for example, 3,4-diaminobenzoic acid and 2,3-diamino-1-methylbenzene,
di- or trihydroxybenzene derivatives such as, for example, resorcinol, resorcinol monomethyl ether, 2-methylresorcinol, 5-methylresorcinol, 2,5-di-methylresorcinol, 2-chlororesorcinol, 4-chloro-resorcinol, pyrogallol and 1,2,4-trihydroxy-benzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-di-hydroxynaphthalene, 1,6-dihydroxynaphthalene, 1,7-dihydroxynaphthalene, 1,8-dihydroxy-naphthalene, 2,7-dihydroxynaphthalene and 2,3-di-hydroxynaphthalene, morpholine derivatives such as, for example, 6-hydroxybenzomorpholine and 6-aminobenzo-morpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxy-indole, pyrimidine derivatives, such as, for example, 4,6-diaminopyrimidine, 4-amino-2,6-dihydroxy-pyrimidine, 2,4-diamino-6-hydroxypyrimidine, 2,4,6-trihydroxypyrimidine, 2-amino-4-methyl-pyrimidine, 2-amino-4-hydroxy-6-methylpyrimidine and 4,6-dihydroxy-2-methylpyrimidine, or methylenedioxybenzene derivatives such as, for example, 1-hydroxy-3,4-methylenedioxybenzene, 1-amino-3,4-methylenedioxybenzene and 1-(2'-hydroxyethyl)amino-3,4-methylenedioxybenzene.

Particularly preferred coupler components according to the invention are 1-naphthol, 1,5-, 2,7- and 1,7-dihydroxynaphthalene, 3-aminophenol, 5-amino-2-methyl-phenol, 2-amino-3-hydroxypyridine, resorcinol, 4-chlororesorcinol, 2-chloro-6-methyl-3-aminophenol, 2-methylresorcinol, 5-methylresorcinol, 2,5-dimethyl-resorcinol and 2,6-dihydroxy-3,4-dimethylpyridine.

Precursors of naturally analogous dyes preferably employed are those indoles and indolines which have at least one hydroxy or amino group, preferably as a substituent on the six-membered ring. These groups can carry further substituents, e.g. in form of an etherification or esterification of the hydroxy group or an alkylation of the amino group. In a second preferred embodiment, the colorants contain at least one indole and/or indoline derivative.

Particularly highly suitable as precursors of naturally analogous hair dyes are derivatives of 5,6-dihydroxy-indoline of the formula (IVa)

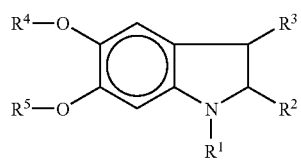

(IVa)

in which, independently of one another,

R$^1$ is hydrogen, a C$_1$–C$_4$-alkyl group or a C$_1$–C$_4$-hydroxyalkyl group, R$^2$ is hydrogen or a —COOH group, where the —COOH group can also be present as a salt with a physiologically tolerable cation, R$^3$ is hydrogen or a C$_1$–C$_4$-alkyl group, R$^4$ is hydrogen, a C$_1$–C$_4$-alkyl group or a group —CO-R$^6$, in which R$^6$ is a C$_1$–C$_4$-alkyl group, and R$^5$ is one of the groups mentioned under R$^4$, and physiologically tolerable salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxy-indoline, N-butyl-5,6-dihydroxyindoline, 5,6-dihydroxy-indoline-2-carboxylic acid, and 6-hydroxyindoline, 6-aminoindoline and 4-aminoindoline.

Particularly to be emphasized within this group are N-methyl-5,6-dihydroxyindoline, N-ethyl-5,6-dihydroxy-indoline, N-propyl-5,6-dihydroxyindoline, N-butyl-5,6-dihydroxyindoline and in particular 5,6-dihydroxy-indoline.

Precursors of naturally analogous hair dyes which are outstandingly suitable are furthermore derivatives of 5,6-dihydroxyindole of the formula (IVb),

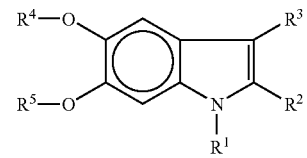

(IVb)

in which, independently of one another,

R$^1$ is hydrogen, a C$_1$–C$_4$-alkyl group or a C$_1$–C$_4$-hydroxyalkyl group, R$^2$ is hydrogen or a —COOH group, where the —COOH group can also be present as a salt with a physiologically tolerable cation, R$^3$ is hydrogen or a C$_1$–C$_4$-alkyl group, R$^4$ is hydrogen, a C$_1$–C$_4$-alkyl group or a group —CO-R$^6$, in which R$^6$ is a C$_1$–C$_4$-alkyl group, and R$^5$ is one of the groups mentioned under R$^4$, and physiologically tolerable salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxy-indole, N-butyl-5,6-dihydroxyindole, 5,6-dihydroxy-indole-2-carboxylic acid, 6-hydroxyindole, 6-amino-indole and 4-aminoindole.

To be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be employed in the colorants employed in the course of the process according to the invention both as free bases and in the form of their physiologically tolerable salts with inorganic or organic acids, e.g. the hydrochlorides, the sulfates and hydrobromides. The indole or indoline derivatives are contained in these customarily in amounts of 0.05–10% by weight, preferably 0.2–5% by weight.

In a further embodiment, it can be preferential according to the invention to employ the indoline or indole derivative in hair colorants in combination with at least one amino acid or one oligopeptide. The amino acid is more advantageously an α-amino acid; very particularly preferred a-amino acids are arginine, ornithine, lysine, serine and histidine, in particular arginine.

In addition to the further dye precursors, the colorants according to the invention can contain one or more direct dyes for tinting. Direct dyes are customarily nitrophenylenediamines, nitroaminophenols, azo dyes, anthraquinones or indophenols. Preferred direct dyes are the compounds known under the international names or trade names HC Yellow 2, HC Yellow 4, HC Yellow 5, HC Yellow 6, Basic Yellow 57, HC Orange 1, Disperse Orange 3, HC Red 1, HC Red 3, HC Red 13, HC Red BN, Basic Red 76, HC Blue 2, HC Blue 12, Disperse Blue 3, Basic Blue 7, Basic Blue 26, Basic Blue 99, HC Violet 1, Disperse Violet 1, Disperse Violet 4, Basic Violet 2, Basic Violet 14, Acid Violet 43, Disperse Black 9, Acid Black 52, Basic Brown 16 and Basic Brown 17, and 1,4-bis(β-hydroxyethyl)amino-2-nitrobenzene, 3-nitro-4-(β-hydroxyethyl)aminophenol, 4-amino-2-nitrodiphenylamine-2'-carboxylic acid, 6-nitro-1,2,3,4-tetrahydroquinoxaline, 2-hydroxy-1,4-naphthoquinone, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene.

The compositions according to the invention as set forth in this embodiment contain the direct dyes preferably in an amount from 0.01 to 20% by weight, based on the total colorant.

The preparations according to the invention can furthermore also contain dyes occurring in nature such as are contained, for example, in henna red, henna neutral, henna black, camomile flower, sandalwood, black tea, alder buckthorn bark, sage, logwood, madder root, Catechu, Sedre and alkanet root.

It is not necessary for the oxidation dye precursors or the direct dyes in each case to be homogeneous compounds. Rather, due to the preparation processes for the individual dyes, still further components can be contained in minor amounts in the hair colorants according to the invention, provided this does not disadvantageously influence the color result or have to be excluded for other reasons, e.g. toxicological reasons.

With respect to the dyes which can be employed in the hair colorants and tinting agents according to the invention, reference is furthermore expressly made to the monograph Ch. Zviak, The Science of Hair Care, chapter 7 (pages 248–250; direct dyes) and chapter 8, pages 264–267; oxidation dye precursors), which appeared as volume 7 of the series "Dermatology" (ed.: Ch., Culnan and H. Maibach), Verlag Marcel Dekker Inc., New York, Basle, 1986, and the "Europäische Inventar der Kosmetik-Rohstoffe" [European inventory of cosmetic raw materials], published by the European Community, obtainable in diskette form from the Bundesverband Deutscher Industrie-und Handelsunternehmen fur Arzneimittel, Reformwaren und Körperpflegemittel e.V., Mannheim.

The colorants according to the invention can furthermore contain all active ingredients, additives and excipients known for such preparations. In many cases, the colorants contain at least one surfactant, where in principle both anionic and zwitterionic, ampholytic, nonionic and cationic surfactants are suitable. In many cases, however, it has proven advantageous to select the surfactants from anionic, zwitterionic or nonionic surfactants.

Suitable anionic surfactants in the preparations according to the invention are all anionic surface-active substances suitable for use on the human body. These are characterized by a water-solubilizing, anionic group such as, for example, a carboxylate, sulfate, sulfonate or phosphate group and a lipophilic alkyl group having approximately 10 to 22 carbon atoms. Glycol or polyglycol ether groups, ester, ether and amide groups, and hydroxyl groups can additionally be contained in the molecule. Examples of suitable anionic surfactants are, in each case in the form of the sodium, potassium and ammonium salts, and the mono-, di- and trialkanolammonium salts having 2 or 3 carbon atoms in the alkanol group, linear fatty acids having 10 to 22 carbon atoms (soaps), ethercarboxylic acids of the formula R-O—$(CH_2—CH_2O)_x$—$CH_2$—COOH, in which R is a linear alkyl group having 10 to 22 carbon atoms and $x=0$ or 1 to 16, acylsarcosides having 10 to 18 carbon atoms in the acyl group, acyltaurides having 10 to 18 carbon atoms in the acyl group, acylisethionates having 10 to 18 carbon atoms in the acyl group, sulfosuccinic acid mono- and dialkyl esters having 8 to 18 carbon atoms in the alkyl group and sulfosuccinic acid monoalkyl polyoxyethyl esters having 8 to 18 carbon atoms in the alkyl group and 1 to 6 oxyethyl groups, linear alkanesulfonates having 12 to 18 carbon atoms, linear alpha-olefinsulfonates having 12 to 18 carbon atoms, alpha-sulfofatty acid methyl esters of fatty acids having 12 to 18 carbon atoms, alkylsulfates and alkyl polyglycol ether sulfates of the formula R-O$(CH_2—CH_2O)_x$—$SO_3H$, in which R is a preferably linear alkyl group having 10 to 18 carbon atoms and $x=0$ or 1 to 12, mixtures of surface-active hydroxysulfonates according to DE-A-37 25 030, sulfated hydroxy-alkylpolyethylene and/or hydroxyalkylenepropylene glycol ethers according to DE-A-37 23 354, sulfonates of unsaturated fatty acids having 12 to 24 carbon atoms and 1 to 6 double bonds according to DE-A-39 26 344, esters of tartaric acid and citric acid with alcohols which are addition products of approximately 2–15 molecules of ethylene oxide and/or propylene oxide to fatty alcohols having 8 to 22 carbon atoms.

Preferred anionic surfactants are alkyl sulfates, alkyl polyglycol ether sulfates and ethercarboxylic acids having 10 to 18 carbon atoms in the alkyl group and up to 12 glycol ether groups in the molecule, and in particular salts of saturated and in particular unsaturated $C_8$–$C_{22}$-carboxylic acids, such as oleic acid, stearic acid, isostearic acid and palmitic acid.

Nonionic surfactants contain, as a hydrophilic group, for example, a polyol group, a polyalkylene glycol ether group or a combination of a polyol and polyglycol ether group. Such compounds are, for example, addition products of 2 to 30 mol of ethylene oxide and/or 0 to 5 mol of propylene oxide to linear fatty alcohols having 8 to 22 carbon atoms, to fatty acids having 12 to 22 carbon atoms and to alkylphenols having 8 to 15 carbon atoms in the alkyl group, $C_{12}$–$C_{22}$-fatty acid mono- and diesters of addition products of 1 to 30 mol of ethylene oxide to glycerol, $C_8$–$C_{22}$-alkylmono- and oligoglycosides and their ethoxylated analogs, and addition products of 5 to 60 mol of ethylene oxide to castor oil and hardened castor oil.

Preferred nonionic surfactants are alkyl polyglycosides of the general formula $R^1O$-$(Z)_x$. These compounds are characterized by the following parameters.

The alkyl radical $R^1$ contains 6 to 22 carbon atoms and can be either linear or branched. Primary linear aliphatic radicals and aliphatic radicals which are methyl-branched in the 2-position are preferred. Such alkyl radicals are, for example, 1-octyl, 1-decyl, 1-lauryl, 1-myristyl, 1-cetyl and 1-stearyl. 1-Octyl, 1-decyl, 1-lauryl, 1-myristyl are particularly preferred. When using "oxo-alcohols" as starting substances, compounds having an odd number of carbon atoms in the alkyl chain predominate.

The alkyl polyglycosides which can be used according to the invention can, for example, contain only a certain alkyl radical $R^1$. Customarily, these compounds, however, are prepared starting from natural fats and oils or mineral oils. In this case, alkyl radicals R present are mixtures corresponding to the starting compounds or corresponding to the respective work-up of these compounds.

Those alkyl polyglycosides are particularly preferred in which $R^1$ consists
essentially of $C_8$- and $C_{10}$-alkyl groups,
essentially of $C_{12}$- and $C_{14}$-alkyl groups,
essentially of $C_8$- to $C_{16}$-alkyl groups or
essentially of $C_{12}$- to $C_{16}$-alkyl groups.

As the sugar unit Z, any desired mono- or oligosaccharides can be employed. Customarily, sugars having 5 or 6 carbon atoms, and the corresponding oligosaccharides are employed. Such sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides which can be used according to the invention contain on average 1.1 to 5 sugar units. Alkyl polyglycosides having x values of 1.1 to 1.6 are preferred. Alkyl glycosides in which x is 1.1 to 1.4 are very particularly preferred.

The alkyl glycosides can, in addition to their surfactant action, also be used to improve the fixing of fragrance components to the hair. The person skilled in the art will thus preferably fall back on this class of substance as a further ingredient of the preparations according to the invention in the case where an action of the perfume oil on the hair exceeding the period of the hair treatment is desired.

The alkoxylated homologs of the alkyl polyglycosides mentioned can also be employed according to the invention. These homologs can on average contain up to 10 ethylene oxide and/or propylene oxide units per alkyl glycoside unit.

Zwitterionic surfactants can furthermore be used, in particular as cosurfactants. Surface-active compounds designated as zwitterionic surfactants are those which carry at least one quaternary ammonium group and at least one $—COO^{(-)}$ or $—SO_3^{(-)}$ group in the molecule. Particularly suitable zwitterionic surfactants are the "betaines", such as the N-alkyl-N,N-dimethylammonium glycinates, for example coconut alkyl dimethylammonium glycinate, N-acylaminopropyl-N,N-dimethylammonium glycinates, for example coconut acylaminopropyl dimethylammonium glycinate, and 2-alkyl-3-carboxyl-methyl-3-hydroxyethylimidazolines in each case having 8 to 18 carbon atoms in the alkyl or acyl group, and coconut acylaminoethylhydroxyethylcarboxymethyl glycinate. A preferred zwitterionic surfactant is the fatty acid amide derivative known under the INCI name Cocamidopropyl Betaine.

Ampholytic surfactants are likewise in particular suitable as cosurfactants. Ampholytic surfactants are understood as meaning those surface-active compounds which aside from a $C_8$–$C_{18}$-alkyl- or acyl group in the molecule contain at least one free amino group and at least one —COOH or —SO$_3$H group and are equipped for the formation of internal salts. Examples of suitable ampholytic surfactants are N-alkylglycines, N-alkyl-propionic acids, N-alkylaminobutyric acids, N-alkyliminodipropionic acids, N-hydroxyethyl-N-alkyl-amidopropylglycines, N-alkyltaurines, N-alkyl-sarcosines, 2-alkylaminopropionic acids and alkylamino-acetic acids in each case having approximately 8 to 18 carbon atoms in the alkyl group. Particularly preferred ampholytic surfactants are N-coconut alkylamino-propionate, coconut acylaminoethylaminopropionate and $C_{12-18}$-acylsarcosine.

According to the invention, the cationic surfactants in particular employed are those of the type consisting of the quaternary ammonium compounds, the ester quats and the amidoamines.

Preferred quaternary ammonium compounds are ammonium halides, in particular chlorides and bromides, such as, alkyltrimethylammonium chlorides, dialkyldimethyl-ammonium chlorides and trialkylmethylammonium chlorides, for example cetyltrimethylammonium chloride, stearyltrimethylammonium chloride, distearyldimethyl-ammonium chloride, lauryldimethylammonium chloride, lauryldimethylbenzylammonium chloride and tricetyl-methylammonium chloride, and also the imidazolium compounds known under the INCI names Quaternium-27 and Quaternium-83. The long alkyl chains of the above-mentioned surfactants preferably have 10 to 18 carbon atoms.

Ester quats are known substances which contain both at least one ester function and at least one quaternary ammonium group as a structural element. Preferred ester quats are quaternized ester salts of fatty acids with triethanolamine, quaternized ester salts of fatty acids with diethanolalkylamines and quaternized ester salts of fatty acids with 1,2-di-hydroxypropyldialkylamines. Such products are marketed, for example, under the trade names Stepantex®, Dehyquart® and Armocare®. The products Armocare® VGH-70, an N,N-bis(2-palmitoyloxyethyl)dimethylammonium chloride, and also Dehyquart® F-75 and Dehyquart® AU-35 are examples of such ester quats.

The alkylamidoamines are customarily prepared by amidation of natural or synthetic fatty acids and fatty acid cuts with dialkylaminoamines. A particularly suitable compound according to the invention from this substance group is the stearamidopropyldimethylamine obtainable commercially under the name Tegoamid® S 18.

Further cationic surfactants which can be used according to the invention are the quaternized protein hydrolyzates.

Likewise suitable according to the invention are cationic silicone oils such as, for example, the commercially obtainable products Q2-7224 (manufacturer: Dow Corning; a stabilized trimethylsilylamodimethicone), Dow Corning 929 emulsion (comprising a hydroxylamino-modified silicone, which is also designated as amodimethicone), SM-2059 (manufacturer: General Electric), SLM-55067 (manufacturer: Wacker), and Abil® Quat 3270 and 3272 (manufacturer: Th. Goldschmidt; diquaternary polydimethylsiloxanes, Quaternium-80).

An example of a quaternary sugar derivative which can be employed as a cationic surfactant is the commercial product Glucquat®100, according to INCI nomenclature a "Lauryl Methyl Gluceth-10 Hydroxypropyl Dimonium Chloride".

The compounds having alkyl groups employed as the surfactant can in each case be homogeneous substances. However, as a rule it is preferred in the preparation of these substances to start out from native vegetable or animal raw materials, such that substance mixtures having different alkyl chain lengths depending on the respective raw material are obtained.

In the case of the surfactants which are addition products of ethylene oxide and/or propylene oxide to fatty alcohols or derivatives of these addition products, both products having a "normal" homolog distribution and those having a concentrated homolog distribution are used. "Normal" homolog distribution is understood here as meaning mixtures of homologs which are obtained in the reaction of fatty alcohol and alkylene oxide using alkali metals, alkali metal hydroxides or alkali metal alkoxides as catalysts. Concentrated homolog distributions are, on the other hand, obtained, if, for example, hydrotalcites, alkaline earth metal salts of ethercarboxylic acids, alkaline earth metal oxides, hydroxides or alkoxides are used as catalysts. The use of products having a concentrated homolog distribution can be preferential.

In addition, the colorants according to the invention can contain further active ingredients, auxiliaries and additives, such as, for example, nonionic polymers such as, for example, vinylpyrrolidone/vinyl acrylate copolymers, poly-vinylpyrrolidone and vinylpyrrolidone/vinyl acetate copolymers and polysiloxanes, cationic polymers such as quaternized cellulose ethers, polysiloxanes having quaternary groups, dimethyldiallylammonium chloride polymers, acrylamide-dimethyldiallylammonium chloride copolymers, dimethylaminoethyl methacrylate-vinylpyrrolidone copolymers quaternized with diethyl sulfate, vinylpyrrolidone-imidazolinium methochloride copolymers and quaternized polyvinyl alcohol, zwitterionic and amphoteric polymers such as, for example, acrylamidopropyltrimethylammonium chloride/acrylate copolymers and octylacrylamide/methyl methacrylate/tert-butylaminoethyl meth-acrylate/2-hydroxypropyl methacrylate copolymers, anionic polymers such as, for example, polyacrylic acids, crosslinked polyacrylic acids, vinyl acetate/crotonic acid copolymers, vinyl-pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickening agents such as agar-agar, guar gum, alginates, xanthan gum, gum arabic, karaya gum, carob bean flour, linseed gums, dextrans, cellulose derivatives, e.g. methylcellulose, hydroxyalkylcellulose and carboxymethylcellulose, starch fractions and derivatives such as amylose, amylopectin and dextrins, clays such as, for example, bentonite or fully synthetic hydro-colloids such as, for example polyvinyl alcohol, structurants such as maleic acid and lactic acid, hair-conditioning compounds such as phospholipids, for example, soybean lecithin, egg lecithin and cephalins, protein hydrolyzates, in particular elastin, collagen, keratin, lactoprotein, soybean protein and wheat protein hydrolyzates, their condensation products with fatty acids, and quaternized protein hydrolyzates, perfume oils, dimethyl isosorbide and cyclodextrins, solvents and solubilizers such as ethanol, isopropanol, ethylene glycol, propylene glycol, glycerol and diethylene glycol, fiber structure-improving active ingredients, in particular mono, di- and oligosaccharides such as, for example, glucose, galactose, fructose, levulose and lactose, quaternized amines such as methyl-1-alkyl-amidoethyl-2-alkylimidazolinium methosulfate antifoams such as silicones, dyes for coloring the composition, antidandruff active ingredients such as piroctone olamine, zinc omadine and climbazole, lightscreens, in particular derivatized benzophenones, cinnamic acid derivatives and triazines, substances for adjusting the pH, such as, for example, customary acids, in particular edible acids and bases, active ingredients such as allantoin, pyrrolidone-carboxylic acids and their salts, and bisabolol, vitamins, provitamins and vitamin precursors, in particular those of the groups A, $B_3$, $B_5$, $B_6$, C, E, F and H, plant extracts such as the extracts of green tea, oak bark, stinging nettle, Hamamelis, hops, camomile, burdock root, horsetail, hawthorn, linden blossom, almond, aloe vera, pine needle, horse chestnut, sandalwood, juniper, coconut, mango, apricot, lime, wheat, kiwi, melon, orange, grapefruit, sage, rosemary, birch, mallow, lady's smock, wild thyme, yarrow, thyme, melissa, restharrow, coltsfoot, hibiscus, meristem, ginseng and ginger root, cholesterol, consistency-imparting agents such as sugar esters, polyol esters or polyol alkyl ethers, fats and waxes such as spermaceti, beeswax, montan wax and paraffins, fatty acid alkanolamides, complexing agents such as EDTA, NTA, β-alanine-diacetic acid and phosphonic acids, swelling agents and penetrants such as glycerol, propylene glycol monoethyl ether, carbonates, hydrogencarbonates, guanidines, ureas, and primary, secondary and tertiary phosphates, opacifying agents such as latex, styrene/PVP and styrene/acrylamide copolymers pearl luster agents such as ethylene glycol mono- and distearate, and PEG-3 distearate, pigments, stabilizers for hydrogen peroxide and other oxidants, propellants such as propane-butane mixtures, $N_2O$, dimethyl ether, $CO_2$ and air, antioxidants.

With respect to further optional components and the amounts of these components employed, reference is made expressly to the relevant handbooks known to the person skilled in the art, e.g. Kh. Schrader, Grundlagen and Rezepturen der Kosmetika [Bases and formulations of cosmetics], 2nd edition, Hüthig Buch Verlag, Heidelberg, 1989.

The compositions according to the invention contain the dye precursors preferably in a suitable aqueous, alcoholic or aqueous-alcoholic carrier. For the purposes of hair coloring, such carriers are, for example, creams, emulsions, gels or surfactant-containing foaming solutions, such as, for example, shampoos, foam aerosols or other preparations which are suitable for application to the hair. It is, however, also conceivable to integrate the dye precursors into a pulverulent or alternatively tablet-form formulation.

Aqueous-alcoholic solutions are understood within the meaning of the present invention as meaning aqueous solutions comprising 3 to 70% by weight of a $C_1$–$C_4$-alcohol, in particular ethanol or isopropanol. The compositions according to the invention can addition-ally contain further organic solvents, such as, for example, methoxybutanol, benzyl alcohol, ethyl diglycol or 1,2-propylene glycol. All water-soluble organic solvents are preferred here.

The actual oxidative dyeing of the fibers can basically be carried out using atmospheric oxygen. Preferably, however, a chemical oxidant is employed, particularly if, in addition to the dyeing, a lightening effect on human hair is desired. Possible oxidants are persulfates, chlorites and in particular hydrogen peroxide or its addition products to urea, melamine and sodium borate. According to the invention, however, the oxidation dye can also be applied to the hair, together with a catalyst which activates the oxidation of the dye precursors, e.g. by means of atmospheric oxygen. Such catalysts are, for example, metal ions, iodides, quinones or certain enzymes.

Suitable metal ions are for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable here. The metal ions can in principle be employed in the form of any desired, physiologically tolerable salt or in the form of a complex compound. Preferred salts are the acetates, sulfates, halides, lactates and tartrates. By use of these metal salts, both the formation of the dyeing can be accelerated and the tint can be specifically influenced.

Suitable enzymes are, for example, peroxidases, which can markedly increase the action of small amounts of hydrogen peroxide. Furthermore, those enzymes are suitable according to the invention which with the aid of atmospheric oxygen directly oxidize the oxidation dye precursors, such as, for example, the laccases, or produce small amounts of hydrogen peroxide in situ and in this manner biocatalytically activate the oxidation of the dye precursors. Particularly suitable catalysts for the oxidation of the dye precursors are the "2-electron oxidoreductases" in combination with the substrates specific therefor, e.g.

pyranose oxidase and, for example, D-glucose or galactose,
glucose oxidase and D-glucose,
glycerol oxidase and glycerol,
pyruvate oxidase and pyruvic acid or its salts,
alcohol oxidase and alcohol (MeOH, EtOH),
lactate oxidase and lactic acid and its salts,
tyrosinase oxidase and tyrosine,
uricase and uric acid or its salts,
choline oxidase and choline,
amino acid oxidase and amino acids.

The actual hair colorant is expediently prepared immediately before application by mixing the preparation of the oxidant with the preparation comprising the dye precursors. The ready-to-use hair coloring preparation resulting in the course of this should preferably have a pH in the range from 6 to 12. The application of the hair colorant in a weakly alkaline medium is particularly preferred. The application temperatures can be in a range between 15 and 40° C. After a time of action of 5 to 45 minutes, the hair colorant is removed from the hair to be colored by rinsing out. Rewashing with a shampoo is unnecessary if a strongly surfactant-containing carrier, e.g. a coloring shampoo, was used.

In particular in the case of hair which is difficult to color, the preparation can be applied to the hair with the dye precursors but also without prior mixing with the oxidation component. After a time of action of 20 to 30 minutes, —optionally after an intermediate rinse—the oxidation component is then applied. After a further time of action of 10 to 20 minutes, the hair is then rinsed and, if desired, reshampooed. In this embodiment, according to a first variant in which the prior application of the dye precursors is intended to bring about a better penetration into the hair, the corresponding composition is adjusted to a pH of approximately 4 to 7. According to a second variant, an atmospheric oxidation is firstly aimed at, the applied composition preferably having a pH of 7 to 10. In the subsequent accelerated reoxidation, the use of acidically adjusted peroxydisulfate solutions as oxidants can be preferential.

The present application secondly relates to the use of the compositions according to the invention for dyeing keratinic fibers.

The present application thirdly relates to a process for dyeing keratinic fibers in which a composition according to the invention is applied to the fibers and rinsed off again after a time of action.

The present invention fourthly relates to p-phenylenediamine derivatives of the formula (I)

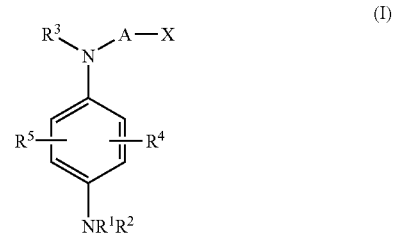

in which
A is a branched or unbranched alkylene group having 1 to 6 carbon atoms, which can carry one or more substituents selected from hydroxy group(s) and halogen atom(s),
X is an optionally substituted imidazolyl radical of the formula (III),

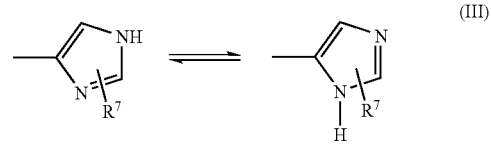

$R^1$, $R^2$ and $R^3$ are, independently of one another, a hydrogen atom, a $C_1$- to $C_4$-alkyl group, a $C_1$- to $C_4$-monohydroxyalkyl group or a $C_2$- to $C_6$-polyhydroxyalkyl group,
$R^4$ and $R^5$ are, independently of one another, a hydrogen atom, a $C_1$- to $C_4$-alkyl group, a $C_1$- to $C_4$-alkoxy group, a $C_1$- to $C_4$-monohydroxyalkyl group, a $C_2$- to $C_4$-polyhydroxyalkyl group or a halogen atom and
$R^7$ is a hydrogen atom, a $C_1$- to $C_4$-alkyl group, a $C_1$- to $C_4$-monohydroxyalkyl group, a $C_2$ to $C_4$-polyhydroxyalkyl group or a halogen atom.

A particularly preferred p-phenylenediamine derivative of the formula (I) is (4-aminophenyl)(2-(imidazol-5-yl)ethyl) amine of the formula (IIIa).

WORKING EXAMPLES

A Preparation of the Compounds

1. Preparation of (4-aminophenyl)(2-(imidazol-5-yl)-ethyl)amine (E1)

1.1 Preparation of (4-nitrophenyl)(2-(imidazol-5-yl)-ethyl) amine 100 ml of DMSO were introduced into a 500 ml three-necked flask and treated with 30.9 g of triethylamine, 18.4 g of histamine dihydrochloride and 14.4 g of 1-fluoro-4-nitrobenzene. The mixture was stirred at 80° C. for 10 h, treated with 20 ml of water and stirred at 80° C. for a further 3 h. Following this, the mixture was allowed to cool to room temperature and poured onto 1 l of ice. The resulting precipitate was filtered off with suction and dried in vacuo at 50° C., 20.8 g of crude product being obtained.

For the purpose of purification, 20.1 g of crude product were boiled three times with 400 ml each of acetone and filtered, the insoluble residue being discarded. The combined acetone solutions were concentrated to a total of 400 ml, and were crystallized out overnight at 5° C. The crystals obtained were dried in vacuo at 50° C.

Yield: 15.2 g (65%).

Melting point: 177–223° C.

1.2 Preparation of (4-aminophenyl)(2-(imidazol-5-yl)-ethyl) amine trihydrochloride (E1)

14.4 g of (4-nitrophenyl)(2-(imidazol-5-yl)ethyl)amine were dissolved in 400 ml of ethanol, treated with 1.0 g of Pd/C (5% strength) and reduced catalytically in a hydrogen shaking apparatus at room temperature and normal pressure. After absorption of hydrogen was complete, the mixture was treated with 100 ml of 2N hydrochloric acid, filtered and concentrated to dryness in vacuo. Following this, it was dried in vacuo at 50° C.

Yield: 18.6 g (96%).

Melting point: >179° C. (decomposition).

2. Preparation of (4-aminophenyl)(3-(imidazol-1-yl)-propyl)amine (E2)

2.1 Preparation of (4-nitrophenyl)(3-(imidazol-1-yl)-propyl) amine 100 ml of DMSO were introduced into a 500 ml three-necked flask and treated with 10.3 g of triethylamine, 12.8 g of 1-(3-aminopropyl)imidazole and 14.4 g of 1-fluoro-4-nitrobenzene. The mixture was stirred at 80° C. for 12 h, cooled to room temperature and subsequently poured onto 1 l of ice. A sample of the resulting oily precipitate was triturated with $H_2O$ until crystallization commenced. A sample of the mixture was seeded with the crystals thus obtained and crystallized at room temperature for 1 h. The resulting precipitate was filtered off with suction, triturated with $H_2O$, filtered off with suction again and rewashed with $H_2O$. For the purpose of purification, the 28 g of moist crude product thus obtained were recrystallized from 250 ml of $H_2O$ and 114 ml of ethanol. The product was dried in vacuo at 50° C.

Yield 20.1 g (81%).

Melting point: 130–132° C.

2.2 Preparation of (4-aminophenyl)(3-(imidazol-1-yl)-propyl)amine trihydrochloride (E2)

14.4 g of (4-nitrophenyl)(3-imidazolylpropyl)amine were dissolved in 400 ml of ethanol, treated with 1.5 g of Pd/C (5% strength) and reduced catalytically in a hydrogen shaking apparatus at room temperature and normal pressure. After absorption of hydrogen was complete, the mixture was treated with 130 ml of 2N hydrochloric acid, filtered and concentrated to dryness in vacuo, being dissolved repeatedly again using ethanol. The oil thus obtained became partially crystalline after 4 days at 5° C. After a treatment with methyl tert-butyl ether, it was decanted off. Following this, the crystals were dried in vacuo at 50° C.

Yield: 22.1 g (90%).

Melting point: >231° C. (decomposition).

3. Preparation of (4-amino-3-methylphenyl)(3-imidazol-1-ylpropyl)amine trihydrochloride (E3)

3.1 Preparation of (4-nitro-3-methylphenyl)(3-(imid-azol-1-yl)propyl)amine 150 ml of dimethyl sulfoxide were introduced into a 500 ml three-necked flask and treated with 22.6 g of triethanolamine (99% strength), 28.7 g of 1-(3-amino-propyl)imidazole (98% strength) and 24.2 g of 5-fluoro-2-nitrotoluene (96% strength). The mixture was stirred at 80° C. for 17 h. Following this, the batch was cooled to room temperature and poured onto 1 l of ice, a yellow oil depositing, which crystallized thoroughly after about 1 h. The precipitate thus resulting was filtered off with suction, washed with water and dried in vacuo at 40° C.

Yield: 38 g (98%).

Melting point: 135–138° C.

3.2 Preparation of (4-amino-3-methylphenyl)(3-imidazol-1-ylpropyl)amine trihydrochloride (E3)

36.4 g of N-(3-imidazol-1-ylpropyl)-4-nitroaniline were suspended in 400 ml of ethanol, treated with 2.5 g of Pd/C (5% strength) and reduced catalytically in a hydrogen shaking apparatus for 3 h. After absorption of hydrogen was complete, the mixture was treated with 200 ml of dilute HCl, the residue was filtered off and the filtrate was concentrated to dryness.

Yield: 42 g (88%).

Melting point: 155° C. (decomposition).

B Dyeings

For the dyeings described below, the developer components E1, E2 and E3 according to the invention described previously were used.

1. Dyeings from a Standard Coloring Cream

For the preparation of the coloring cream, 50 g of a cream base were weighed into a 250 ml beaker and melted at 80° C. The cream base used had the following composition:

| | |
|---|---|
| Hydrenol ® D[1] | 17.0% by weight |
| Lorol ® tech.[2] | 4.0% by weight |
| Texapon ® NSO[3] | 40.0% by weight |
| Dehyton ® K[4] | 25.0% by weight |
| Eumulgin ® B2[5] | 1.5% by weight |
| Water | 12.5% by weight |

[1]$C_{16-18}$-fatty alcohol (INCI name: Cetearyl alcohol) (Cognis)
[2]$C_{12-18}$-fatty alcohol (INCI name: Coconut alcohol) (Cognis)
[3]lauryl ether sulfate, sodium salt (about 27.5% active substance; INCI name: Sodium Laureth Sulfate) (Cognis)
[4]N,N-dimethyl-N-($C_{8-18}$-coconutamidopropyl)ammonium acetobetaine (about 30% active substance; INCI name: Aqua (Water), Cocamidopropyl Betaine) (Cognis)
[5]cetylstearyl alcohol having about 20 EO units (INCI name: Ceteareth-20) (Cognis)

The dye precursors were in each case suspended separately in distilled water or dissolved with warming. Subsequently, ammonia (<1 ml; 25% strength ammonia solution) was added until the pH was between 9 and 10. A solution resulted by the addition of ammonia.

The dissolved dye precursors were incorporated successively into the hot cream. Subsequently, it was made up to 97 g with distilled water and a pH of 9.5 was set with ammonia. After making up to 100 g with distilled water, the batch was stirred until cold (<30° C.), a homogeneous cream resulting.

The cream was diluted as follows for the different dyeings:

| | |
|---|---|
| Atmospheric oxidation: | 25 g of cream + 25 g of distilled water |
| Oxidation using 1% by weight of $H_2O_2$ | 25 g of cream + 25 g of aqueous 1% strength by weight $H_2O_2$ solution |
| Oxidation using 3% by weight $H_2O_2$ | 25 g of cream + 25 g of aqueous 3% strength by weight $H_2O_2$ solution |
| Oxidation using 9% by weight of $H_2O_2$ | 25 g of cream + 25 g of aqueous 9% strength by weight $H_2O_2$ solution |

To each of the mixtures thus obtained was added a strand of hair (turned 80% gray; 330 mg to 370 mg weight). Subsequently, the mixtures and the strands of hair were in each case added to a watch-glass and the strands of hair were well embedded into the coloring creams. After 30 minutes' (±1 minute) time of action at room temperature, the strands of hair were removed and washed with an aqueous Texapon® EVR solution[6] until the excess of dye was removed. The strands of hair were dried in air and their color shade was determined under a daylight lamp (dye testing apparatus HE240A) and noted (Taschenlexikon der Farben [Pocket encyclopaedia of dyeing], A. Kornerup and J. H. Wanscher, 3rd unchanged edition 1981, MUSTER-SCHMIDT Verlag; Zurich, Göttingen).

[6] Lauryl ether sulfate sodium salt with special additions (about 34 to 37% active substance content; INCI name: Sodium Lauryl Sulfate, Sodium Laureth Sulfate, Lauramide MIPA, Cocamide MEA, Glycol Stearate, Laureth-10) (Cognis)

The results obtained in the dyeing investigations are listed in the tables below.

1.1 Dyeings with Couplers

In the case of the following dyeings, the developer components according to the invention were employed in a molar ratio of 1:1 to the coupler components. In each case, 1/400 mol of the developer or coupler component was, employed.

The following coupler components were employed:
K1: resorcinol
K2: 3-amino-6-methoxy-2-(methylamino)pyridine×2HCl
K3: 5-amino-2-methylphenol
K4: 2-amino-3-hydroxypyridine
K5: 1,3-bis(2,4-diaminophenoxy)propane×4HCl
K6: 2,7-dihydroxynaphthalene
K7: 1-hydroxynaphthalene 1.1.1. Dyeings with Atmospheric Oxidation

| | Developer | |
|---|---|---|
| Coupler | E1 | E2 |
| K1 | olive brown | nougat-colored |
| K2 | dirty-gray | olive brown |
| K3 | crimson-gray | gray-brown |
| K4 | purple-gray | purple-gray |
| K5 | gray-blue | dull blue |
| K6 | flax yellow | brown-orange |

1.1.2 Dyeings with 1% Strength Aqueous $H_2O_2$ Solution

| | Developer | |
|---|---|---|
| Coupler | E1 | E2 |
| K1 | gray-brown | negro brown |
| K2 | blue-black | blue-black |
| K3 | dark violet | dark violet |
| K4 | dark crimson | dark crimson |
| K5 | blue-black | blue-black |
| K6 | earth-brown | nutria |
| K7 | not determined | navy blue |

1.1.3 Dyeings with 3% Strength Aqueous $H_2O_2$ Solution

| | Developer |
|---|---|
| Coupler | E3 |
| K1 | olive brown |
| K2 | dark green |
| K3 | dark violet |
| K4 | teak-colored |
| K5 | dark blue |
| K6 | olive brown |

1.1.4 Dyeings with 9% Strength Aqueous $H_2O_2$ Solution

| | Developer | |
|---|---|---|
| Coupler | E1 | E2 |
| K1 | brown-gray | bister |
| K2 | ink blue | blue-gray |
| K3 | dark violet | dark violet |
| K4 | red-brown | dark brown |
| K5 | blue-black | blue-black |
| K6 | mouse-gray | olive |

1.2 Dyeings of the Developer E2 According to the Invention with a Further Developer and a Coupler Component In the following dyeings, the quantitative ratios of the various components were selected in such a way that the ratio of the two developer components was 1:1 and the ratio of the sum of the developer components to the coupler component was likewise 1:1. In total, in each case 1/400 mol of the developer components and 1/400 mol of the coupler component were employed. The coupler components are defined as indicated above.

The following further developer components were employed:
E4: 1-(β-hydroxyethyl)-2,5-diaminobenzene. $H_2SO_4$
E5: 3-methyl-4-aminophenol
E6: 2,4,5,6-tetraaminopyrimidine. $H_2SO_4$
E7: 1-(β-hydroxyethyl)-4,5-diaminopyrazole. $H_2SO_4$ 1.2.1 Dyeings with Atmospheric Oxidation

| | Further developer component | | | |
|---|---|---|---|---|
| Coupler | E4 | E5 | E6 | E7 |
| K1 | brown-orange | nougat-colored | light brown | dull red |
| K2 | mouse gray | olive brown | dark green | brown-gray |

-continued

| Coupler | Further developer component | | | |
|---|---|---|---|---|
| | E4 | E5 | E6 | E7 |
| K3 | brown-gray | gray-brown | dull violet | red-brown |
| K4 | brown-gray | mouse gray | brown-gray | brown-gray |
| K5 | Blue-gray | blue-gray | deep blue | dark blue |
| K6 | nougat-colored | flax yellow | clay-colored | nougat-colored |

1.2.2 Dyeings with 1% Strength Aqueous $H_2O_2$ Solution

| Coupler | Further developer component | | | |
|---|---|---|---|---|
| | E4 | E5 | E6 | E7 |
| K1 | negro brown | hair brown | dark brown | violet brown |
| K2 | Blue-black | dark green | jungle green | dark violet |
| K3 | Dark purple | gray-ruby | dark violet | violet brown |
| K4 | red-brown | red-brown | gray-brown | port wine red |
| K5 | Blue-black | blue-black | blue-black | dark violet |
| K6 | brown-gray | fallow | bronzino | hair brown |

1.2.3 Dyeings with 9% Strength Aqueous $H_2O_2$ Solution

| Coupler | Further developer component | | | |
|---|---|---|---|---|
| | E4 | E5 | E6 | E7 |
| K1 | chocolate brown | olive brown | dark brown | liver brown |
| K2 | Blue-gray | nickel green | dark green | dark violet |
| K3 | Dark purple | gray-ruby | dark violet | violet-brown |
| K4 | somali | fawn | brown | dark brown |
| K5 | Blue-black | blue-black | dark brown | dark violet |
| K6 | nutria | fallow | olive brown | olive brown |

1.3 Dyeings of the Developer E1 According to the Invention with a Further Developer and Standard Couplers In the following dyeings, the quantitative ratios of the various components were selected in such a way that the ratio of the two developer components was 1:1 and the ratio of the sum of the developer components to the coupler component was likewise 1:1. In total, in each case 1/400 mol of the developer components and 1/400 mol of the coupler component were employed.

The developer components and coupler components are defined as indicated above.

1.3.1 Dyeings with 6% Strength Aqueous $H_2O_2$ Solution

| Coupler | Further developer component | | | |
|---|---|---|---|---|
| | E4 | E5 | E6 | E7 |
| K1 | brown-beige | mouse gray | dark brown | red-brown |
| K2 | ink blue | dark green | olive | blue-black |
| K3 | Dark purple | violet brown | burgundy red | violet-brown |
| K4 | somali | fawn | somali | red-brown |

-continued

| Coupler | Further developer component | | | |
|---|---|---|---|---|
| | E4 | E5 | E6 | E7 |
| K5 | Blue-black | blue-black | dark green | dark violet |
| K6 | olive brown | olive | olive | olive brown |

2. Dyeing from Market-relevant Color Creams

The following formulations were mixed with an oxidant preparation (formulation 2.14) in the weight ratio 1:1 before application. The resulting application preparations were in each case applied to strands of hair (Kerling natural white), left there for 30 minutes at 32° C. and subsequently rinsed out thoroughly.

Formulation 2.1

| Raw material | Amount in % by weight |
|---|---|
| Fatty alcohol mixture $C_{12}$–$C_{18}$ | 6.0 |
| Eumulgin ® B2 | 0.5 |
| Texapon ® NSO | 10.0 |
| Dehyton ® K | 5.0 |
| Polymer JR ® 400[7] | 0.4 |
| Gafquat ® 755 N[8] | 0.2 |
| Celquat ® L 200[9] | 0.2 |
| Ascorbic acid | 0.4 |
| Ammonium sulfate | 0.5 |
| E2 (according to the invention) | 0.14 |
| Bis(5-amino-2-hydroxyphenyl)-methane dihydrochloride | 0.031 |
| 4-Amino-3-methylphenol | 0.011 |
| 2-Amino-3-hydroxypyridine | 0.006 |
| 3-Amino-2,4-dichlorophenol | 0.012 |
| 1,3-Bis(2',4'-diaminophenoxy)-propane tetrahydrochloride | 0.0004 |
| 1,3-Bis(2',4'-diamiophenyl)-propane tetrahydrochloride | 0.0004 |
| Resorcinol | 0.015 |
| 4-Chlororesorcinol | 0.015 |
| 3-Aminophenol | 0.003 |
| Ammonia, 25% strength | to pH 9.8 |
| Water | to 100 |
| Color result | pearl gray |

Formulation 2.2

| Raw material | Amount in % by weight |
|---|---|
| Fatty alcohol mixture $C_{12}$–$C_{18}$ | 6.0 |
| Eumulgin ® B2 | 0.5 |
| Texapon ® NSO | 10.0 |
| Dehyton ® K | 5.0 |
| Polymer JR ® 400 | 0.4 |
| Gafquat ® 755 | 0.2 |
| Celquat ® L 200 | 0.2 |
| Ascorbic acid | 0.4 |
| Ammonium sulfate | 0.5 |
| E3 (according to the invention) | 1.21 |
| Bis(5-amino-2-hydroxyphenyl)methane dihydrochloride | 1.09 |
| 4-Amino-2-aminomethylphenol dihydrochloride | 0.05 |
| 4-Amino-2-((diethylamino)methyl)phenol dihydrochloride | 0.05 |
| 4-Amino-3-methylphenol | 0.30 |
| 2-Amino-4-methylphenol | 0.02 |

-continued

| Raw material | Amount in % by weight |
| --- | --- |
| 2-Amino-3-hydroxypyridine | 0.12 |
| 5-Amino-4-chloro-2-methylphenol | 0.12 |
| 2-Methylresorcinol | 0.24 |
| 4-Chlororesorcinol | 0.12 |
| 3-Aminophenol | 0.24 |
| 5,6-Dihydroxyindoline hydrobromide | 0.06 |
| Ammonia, 25% strength | to pH 9.8 |
| Water | to 100 |
| Color result | cocoa-brown |

Formulation 2.3

| Raw material | Amount in % by weight |
| --- | --- |
| Fatty alcohol mixture $C_{12}$–$C_{18}$ | 6.0 |
| Eumulgin ® B2 | 0.5 |
| Texapon ® NSO | 10.0 |
| Dehyton ® K | 5.0 |
| Polymer JR ® 400 | 0.4 |
| Gafquat ® 755 | 0.2 |
| Celquat ® L 200 | 0.2 |
| Ascorbic acid | 0.4 |
| Ammonium sulfate | 0.5 |
| E1 (according to the invention) | 0.03 |
| Bis(5-amino-2-hydroxyphenyl)methane dihydrochloride | 1.36 |
| p-Toluylenediamine sulfate | 0.03 |
| p-Phenylenediamine dihydrochloride | 0.03 |
| 2-(2'-Hydroxyethyl)-p-phenylenediamine sulfate | 0.07 |
| N,N-Bis(2'-hydroxyethyl-p-phenylenediamine sulfate | 0.07 |
| 4-Amino-3-methylphenol | 0.55 |
| 2-Amino-5-methylphenol | 0.01 |
| 2-Amino-4-chlorophenol | 0.02 |
| 4-Amino-2-chlorophenol | 0.01 |
| 2-Amino-3-hydroxypyridine | 0.5 |
| 5-Amino-2-methylphenol | 0.03 |
| 5-(2'-Hydroxyethyl)amino-2-methylphenol | 0.01 |
| 3-Amino-2-chloro-6-methylphenol | 0.02 |
| 6-Hydroxyindole | 0.1 |
| 1,2,3,4-Tetrahydro-6-nitroquinoxaline | 0.05 |
| HC Yellow 5 | 0.03 |
| HC Red 1 | 0.01 |
| 4-Amino-2-nitrodiphenylamine-2'-carboxylic acid | 0.01 |
| Ammonia, 25% strength | to pH 9.8 |
| Water | to 100 |
| Color result | leather brown |

Formulation 2.4

| Raw material | Amount in % by weight |
| --- | --- |
| Fatty alcohol mixture $C_{12}$–$C_{18}$ | 10.0 |
| Texapon ® K14 S70C[10] | 2.5 |
| Plantaren ® 1200 UP[11] | 2.0 |
| Akypo Soft ® 45 NV[12] | 12.0 |
| Eutanol ® G[13] | 1.0 |
| Eumulgin ® B1[14] | 0.5 |
| Eumulgin ® B2 | 0.5 |
| Polymer W 37194[15] | 2.0 |
| Cosmedia Guar ® C261[16] | 0.2 |
| Mirapol ® A15[17] | 0.5 |
| Ascorbic acid | 0.4 |
| Ammonium sulfate | 0.5 |

-continued

| Raw material | Amount in % by weight |
| --- | --- |
| E1 (according to the invention) | 0.030 |
| Bis(5-amino-2-hydroxyphenyl)methane dihydrochloride | 0.037 |
| 2-(2'-Hydroxyethyl)-p-phenylenediamine sulfate | 0.022 |
| 1-Naphthol | 0.015 |
| 2-Methyl-1-naphthol | 0.022 |
| 1,5-Dihydroxynaphthalene | 0.005 |
| 3-Amino-2-methylamino-6-methoxypyridine | 0.003 |
| 2-Methylresorcinol | 0.009 |
| Ammonia, 25% strength | to pH 9.8 |
| Water | to 100 |
| Color result | twilight gray |

Formulation 2.5

| Raw material | Amount in % by weight |
| --- | --- |
| Fatty alcohol mixture $C_{12}$–$C_{18}$ | 10.0 |
| Texapon ® K14 S70C | 2.5 |
| Plantaren ® 1200 UP | 2.0 |
| Akypo Soft ® 45 NV | 12.0 |
| Eutanol ® G | 1.0 |
| Eumulgin ® B1 | 0.5 |
| Eumulgin ® B2 | 0.5 |
| Polymer W 37194 | 2.0 |
| Cosmedia Guar ® C261 | 0.2 |
| Mirapol ® A15 | 0.5 |
| Ascorbic acid | 0.4 |
| Ammonium sulfate | 0.5 |
| E2 (according to the invention) | 0.92 |
| Bis(5-amino-2-hydroxyphenyl)methane dihydrochloride | 0.124 |
| p-Toluylenediamine sulfate | 0.59 |
| 4-Amino-2-aminomethylphenol dihydrochloride | 0.01 |
| 4-Amino-3-methylphenol | 0.077 |
| 2,4,5,6-Tetraaminopyrimidine sulfate | 0.08 |
| 4-Hydroxy-2,5,6-triaminopyrimidine sulfate | 0.02 |
| 4,5-Diamino-1-(2'-hydroxyethyl)pyrazole sulfate | 0.02 |
| 2,7-Dihydroxynaphthalene | 0.035 |
| 2-Amino-3-hydroxypyridine | 0.44 |
| 3-Amino-2-methylamino-6-methoxypyridine | 0.002 |
| 2,6-Dihydroxy-3,4-dimethylpyridine | 0.002 |
| Resorcinol | 0.12 |
| 2-Methylresorcinol | 0.72 |
| 3-Aminophenol | 0.007 |
| 4-Amino-2-nitrodiphenylamine-2'-carboxylic acid | 0.05 |
| 2-Ethylamino-4-nitro-6-chlorophenol | 0.05 |
| Ammonia, 25% strength | to pH 9.8 |
| Water | to 100 |
| Color result | dark ruby |

Formulation 2.6

| Raw material | Amount in % by weight |
| --- | --- |
| Fatty alcohol mixture $C_{12}$–$C_{18}$ | 10.0 |
| Texapon ® K14 S70C | 2.5 |
| Plantaren ® 1200 UP | 2.0 |
| Akypo Soft ® 45 NV | 12.0 |
| Eutanol ® G | 1.0 |
| Eumulgin ® B1 | 0.5 |

-continued

| Raw material | Amount in % by weight |
| --- | --- |
| Eumulgin ® B2 | 0.5 |
| Polymer W 37194 (Stockhausen) | 2.0 |
| Cosmedia Guar ® C261 | 0.2 |
| Mirapol ® A15 | 0.5 |
| Ascorbic acid | 0.4 |
| Ammonium sulfate | 0.5 |
| Akypo Soft ® 45 NV | 12.0 |
| E3 (according to the invention) | 0.03 |
| Bis(5-amino-2-hydroxyphenyl)methane dihydrochloride | 2.40 |
| 4-Amino-2-((diethylamino)methyl)phenol dihydrochloride | 0.18 |
| 3-Amino-2-methylamino-6-methoxypyridine | 2.04 |
| 2,6-Dihydroxy-3,4-dimethylpyridine | 0.01 |
| 3,5-Diamino-2,6-dimethoxypyridine | 0.02 |
| 2-Ethylamino-4-nitro-6-chlorophenol | 0.07 |
| HC Red BN[18] | 0.2 |
| 5,6-Dihydroxyindoline hydrobromide | 0.12 |
| Ammonia, 25% strength | to pH 9.8 |
| Water | to 100 |
| Color result | henna red |

Formulations 2.7

| Raw material | Amount in % by weight |
| --- | --- |
| Fatty alcohol mixture $C_{12}$–$C_{18}$ | 8.0 |
| Texapon ® NSO | 2.0 |
| Dehyton ® K | 1.0 |
| Potassium oleate | 2.0 |
| Potassium isostearate | 2.0 |
| Myristic acid | 1.0 |
| Eumulgin ® B2 | 0.5 |
| Custofac Diacid ® H240[19] | 2.0 |
| Merquat ® 550[20] | 0.2 |
| Luviquat ® FC370[21] | 0.1 |
| Merquat ® 280[22] | 0.1 |
| Gafquat ® HS-100[23] | 0.1 |
| Ascorbic acid | 0.4 |
| Texapon ® NSO | 2.0 |
| Dehyton ® K | 1.0 |
| Potassium oleate | 2.0 |
| Ammonium sulfate | 0.5 |
| E1 (according to the invention) | 0.05 |
| Bis(5-amino-2-hydroxyphenyl)-methane dihydrochloride | 2.33 |
| 5-Amino-2-methylphenol | 0.6 |
| 5-(2'-Hydroxyethyl)amino-2-methylphenol | 0.3 |
| 3-Amino-2-chloro-6-methylphenol | 0.5 |
| Ammonia, 25% strength | to pH 9.8 |
| Water | to 100 |
| Color result | red gold |

Formulation 2.8

| Raw material | Amount in % by weight |
| --- | --- |
| Fatty alcohol mixture $C_{12}$–$C_{18}$ | 8.0 |
| Texapon ® NSO | 2.0 |
| Dehyton ® K | 1.0 |
| Potassium oleate | 2.0 |
| Potassium isostearate | 2.0 |
| Myristic acid | 1.0 |
| Eumulgin ® B2 | 0.5 |
| Custofac Diacid ® H240 | 2.0 |
| Merquat ® 550 | 0.2 |
| Luviquat ® FC 370 | 0.1 |

-continued

| Raw material | Amount in % by weight |
| --- | --- |
| Merquat ® 280 | 0.1 |
| Gafquat ® HS-100 | 0.1 |
| Ascorbic acid | 0.4 |
| Ammonium sulfate | 0.5 |
| E2 (according to the invention) | 0.37 |
| Bis(5-amino-2-hydroxyphenyl)methane dihydrochloride | 1.24 |
| p-Toluylenediamine sulfate | 0.15 |
| 2-(2'-Hydroxyethyl)-p-phenylenediamine sulfate | 0.10 |
| 2-Amino-4-methylphenol | 0.01 |
| 4,5-Diamino-1-(2'-hydroxyethylpyrazole) sulfate | 0.24 |
| 2,7-Dihydroxynaphthalene | 0.10 |
| 5-Amino-2-methylphenol | 0.15 |
| 5-(2'-Hydroxyethyl) amino-2-methylphenol | 0.44 |
| 5-Amino-4-chloro-2-methylphenol | 0.1 |
| Resorcinol | 0.04 |
| 2-Methylresorcinol | 0.08 |
| 4-Chlororesorcinol | 0.05 |
| Ammonia, 25% strength | to pH 9.8 |
| Water | to 100 |
| Color result | maroon |

Formulation 2.9

| Raw material | Amount in % by weight |
| --- | --- |
| Fatty alcohol mixture $C_{12}$–$C_{18}$ | 8.0 |
| Texapon ® NSO | 2.0 |
| Dehyton ® K | 1.0 |
| Potassium oleate | 2.0 |
| Potassium isostearate | 2.0 |
| Myristic acid | 1.0 |
| Eumulgin ® B2 | 0.5 |
| Custofac Diacid ® H240 | 2.0 |
| Merquat ® 550 | 0.2 |
| Luviquat ® FC 370 | 0.1 |
| Merquat ® 280 | 0.1 |
| Gafquat ® HS-100 | 0.1 |
| Ascorbic acid | 0.4 |
| Ammonium sulfate | 0.5 |
| E3 (according to the invention) | 0.09 |
| Bis(5-amino-2-hydroxyphenyl)methane dihydrochloride | 0.038 |
| p-Phenylenediamine dihydrochloride | 0.10 |
| 4-Amino-2-aminomethylphenol | 0.3 |
| 4-Amino-2-((diethylamino)methyl)phenol dihydrochloride | 0.8 |
| 4-Amino-3-methylphenol | 0.011 |
| 2,4,5,6-Tetraaminopyrimidine sulfate | 0.80 |
| 4-Hydroxy-3,5,6-triaminopyrimidine | 0.08 |
| 2,7-Dihydroxynaphthalene | 0.33 |
| 5-(2'-Hydroxyethyl)amino-2-methylphenol | 0.015 |
| 5-Amino-4-chloro-2-methylphenol | 0.030 |
| Resorcinol | 0.044 |
| 2-Methylresorcinol | 0.25 |
| 3-Aminophenol | 0.004 |
| 4-Amino-2-nitro-diphenylamine-2'-carboxylic acid | 0.15 |
| 4-Amino 3-nitrophenol | 0.25 |
| Ammonia, 25% strength | to pH 9.8 |
| Water | to 100 |
| Color result | fox red |

Formulation 2.10

| Raw material | Amount in % by weight |
|---|---|
| Fatty alcohol mixture $C_{12}$–$C_{18}$ | 8.0 |
| Texapon ® NSO | 2.0 |
| Dehyton ® K | 1.0 |
| Potassium oleate | 2.0 |
| Potassium isostearate | 2.0 |
| Myristic acid | 1.0 |
| Eumulgin ® B2 | 0.5 |
| Custofac Diacid ® H240 | 2.0 |
| Merquat ® 550 | 0.2 |
| Luviquat ® FC 370 | 0.1 |
| Merquat ® 280 | 0.1 |
| Gafquat ® HS-100 | 0.1 |
| Ascorbic acid | 0.4 |
| Ammonium sulfate | 0.5 |
| E1 (according to the invention) | 0.02 |
| E2 (according to the invention) | 0.02 |
| E3 (according to the invention) | 0.02 |
| Bis(5-amino-2-hydroxyphenyl)methane dihydrochloride | 1.47 |
| 4-Amino-3-methylphenol | 0.1 |
| 3-Amino-2-methylamino-6-methoxypyridine | 0.05 |
| 2,6-Dihydroxy-3,4-dimethylpyridine | 0.01 |
| 3,5-Diamino-2,6-dimethoxypyridine | 0.05 |
| 5-Amino-2-methylphenol | 0.40 |
| 5-(2'-Hydroxyethyl) amino-2-methylphenol | 0.30 |
| 3-Amino-2-chloro-6-methylphenol | 0.06 |
| 3-Amino-2,4-dichlorophenol | 0.04 |
| 2,4-Diaminophenoxyethanol sulfate | 0.01 |
| 1,3-Bis(2',4'-diaminophenoxy)propane tetrahydrochloride | 0.1 |
| 1,3-Bis(2',4'-diamiphenyl) propane tetrahydrochloride | 0.2 |
| 4-Hydroxyindole | 0.1 |
| Ammonia, 25% strength | to pH 9.8 |
| Water | to 100 |
| Color result | somali |

Formulation 2.11

| Raw material | Amount in % by weight |
|---|---|
| Fatty alcohol mixture $C_{12}$–$C_{18}$ | 10.0 |
| Eumulgin ® B1 | 1.0 |
| Eumulgin ® B2 | 1.0 |
| Texapon ® NSO | 3.0 |
| Dehyton ® K | 1.0 |
| Akypo ® RLM 45 N[24] | 3.0 |
| Aminoxid ® WS 35[25] | 0.5 |
| Merquat ® 100[26] | 0.05 |
| Merquat ® 280 | 0.05 |
| Polymer JR ® 400 | 0.05 |
| Mirapol ® A15 | 0.05 |
| Silkall ® 100[27] | 0.5 |
| Ammonium sulfate | 0.4 |
| Turpinal ® SL[28] | 0.2 |
| Nutrilan Keratin ® W[29] | 1.0 |
| Sodium silicate 40/42 | 0.5 |
| E1 (according to the invention) | 0.08 |
| 2,4,5,6-Tetraaminopyrimidine sulfate | 1.0 |
| 2,6-Bis(2'-hydroxyethylamino)-toluene | 0.08 |
| p-Toluylenediamine sulfate | 0.10 |
| Perfume | 0.2 |
| 2-Methylresorcinol | 0.59 |
| HC Red B54[30] | 0.05 |
| HC Red BN | 0.05 |
| 1,4-Diamino-2-nitrobenzene | 0.2 |
| Acid Red 52 | 0.05 |
| Ammonia, conc | to pH 10 |
| Water | to 100 |
| Color result | strawberry red |

Formulation 2.12

| Raw material | Amount in % by weight |
|---|---|
| Fatty alcohol mixture $C_{12}$–$C_{18}$ | 10.0 |
| Eumulgin ® B1 | 1.0 |
| Eumulgin ® B2 | 1.0 |
| Texapon ® NSO | 3.0 |
| Dehyton ® K | 1.0 |
| Akypo RLM ® 45 N | 3.0 |
| Aminoxid ® WS 35 | 0.5 |
| Merquat ® 100 | 0.05 |
| Merquat ® 280 | 0.05 |
| Polymer JR ® 400 | 0.05 |
| Mirapol ® A 15 | 0.05 |
| Silkall ® 100 | 0.5 |
| Ammonium sulfate | 0.4 |
| Turpinal ® SL | 0.2 |
| Nutrilan Keratin ® W | 1.0 |
| Sodium silicate 40/42 | 0.5 |
| Perfume | 0.2 |
| E2 (according to the invention) | 0.30 |
| p-Toluylenediamine sulfate | 0.22 |
| 5-Amino-2-methylphenol | 0.25 |
| 3-Amino-2-chloro-6-methylphenol | 0.07 |
| Acid Red 33 | 0.05 |
| Water | to 100 |
| Ammonia, conc | to pH 10 |
| Color result | magenta |

Formulation 2.13

| Raw material | Amount in % by weight |
|---|---|
| Fatty alcohol mixture $C_{12}$–$C_{18}$ | 10.0 |
| Eumulgin ® B1 | 1.0 |
| Eumulgin ® B2 | 1.0 |
| Texapon ® NSO | 3.0 |
| Dehyton ® K | 1.0 |
| Akypo RLM ® 45 N | 3.0 |
| Aminoxid WS ® 35 | 0.5 |
| Merquat ® 100 | 0.05 |
| Merquat ® 280 | 0.05 |
| Polymer JR ® 400 | 0.05 |
| Mirapol ® A 15 | 0.05 |
| Silkall ® 100 | 0.5 |
| Ammonium sulfate | 0.4 |
| Turpinal ® SL | 0.2 |
| Nutrilan Keratin ® W | 1.0 |
| Sodium silicate 40/42 | 0.5 |
| Perfume | 0.2 |
| E3 (according to the invention) | 0.31 |
| p-Toluylenediamine sulfate | 0.16 |
| 4-Amino-3-methylphenol | 0.43 |
| 2,7-Dihydroxynaphthalene | 0.02 |
| Resorcinol | 0.17 |
| 5-Amino-2-methylphenol | 0.14 |
| 4-Amino-2-nitrodiphenyl-amine-2'-carboxylic acid | 0.05 |
| 6-Nitro-1,2,3,4-tetrahydroquinoxaline | 0.03 |
| Rodol ® 9R[31] | 0.02 |
| Ammonia, conc. | To pH 10 |
| Water | to 100 |
| Color result | fawn |

Formulation 2.14

| Raw material | Amount in % by weight |
| --- | --- |
| Dipicolinic acid | 0.10 |
| Sodium pyrophosphate | 0.03 |
| Turpinal ® SL | 1.50 |
| Texapon ® N28[32] | 2.00 |
| Dow Corning ® DB 110A[33] | 0.07 |
| Aculyn ® 33[34] | 12.00 |
| Hydrogen peroxide, 50% strength | 12.00 |
| Ammonia, 25% strength | 0.60 |
| Water | to 100 |

The commercial products employed in the context of the examples have the following ingredients:

7 quaternized hydroxyethylcellulose (INCI name: Polyquaternium-10) (Amerchol)

8 quaternized vinylpyrrolidone-dimethylaminoethyl methacrylate copolymer (about 19–21% active substance content; INCI name: Polyquaternium-11) (ISP)

9 quaternized cellulose derivative (INCI name: Polyquaternium-4) (National Starch)

10 lauryl myristyl ether sulfate sodium salt (about 68 to 73% active substance content; INCI name: Sodium Myreth Sulfate) (Cognis)

11 $C_{12-16}$-fatty alcohol 1,4-glucoside (about 50–53% active substance content; INCI name: Lauryl Glucoside, Aqua (Water)) (Cognis)

12 $C_{12-14}$-fatty alcohol-4.5 EO-acetic acid sodium salt (at least 21% active substance content; INCI name: Sodium Laureth-6 Carboxylate) (Kao)

13 2-octyldodecyl alcohol (INCI name: Octyldodecanol) (Cognis)

14 cetylstearyl alcohol having about 12 EO units (INCI name: Ceteareth-12) (Cognis)

15 acrylic acid sodium salt-acrylamidopropyl-trimethylammonium chloride copolymer preserved with Phenonip (about 19–21% active substance, INCI name: Acrylamidopropyl-Trimonium Chloride/Acrylates Copolymer) (Stockhausen)

16 guar hydroxypropyltrimethylammonium chloride (INCI name: Guar Hydroxypropyltrimonium Chloride) (Cognis)

17 poly[N-(3-(dimethylammonium)propyl]-N'-[3-ethylenoxyethylenedimethylammonium)propyl]urea dichloride (about 64% active substance content; INCI name: Polyquaternium-2) (Rhodia)

18 4-[(3-hydroxypropyl)amino]-3-nitrophenol 19 4-hexyl-5(6)-carboxy-2-cyclohexene-1-octanoic acid potassium salt (about 41% active substance content) (Westvaco Chemicals)

20 dimethyldiallylammonium chloride-acrylamide copolymer (about 8.1–9.1% active substance content; INCI name: Polyquaternium-7) (Ondeo-Nalco)

21 vinylimidazolium methochloride-vinylpyrrolidone copolymer (30:70) (about 38–42% active substance content; INCI name: Polyquaternium-16) (BASF)

22 dimethyldiallylammonium chloride-acrylic acid copolymer (about 35% active substance in water, INCI name: Polyquaternium-22) (Ondeo-Nalco)

23 vinylpyrrolidone-methacrylamidopropyltrimethyl-ammonium chloride copolymer (about 19–21% active substance content in water, INCI name: Polyquaternium-28) (Gaf Corp.)

24 $C_{12-14}$-fatty alcohol-4.5-EO-acetic acid sodium salt (about 80–84% active substance content in water and NaCl; INCI name: Sodium Laureth-6 Carboxylate) (Kao)

25 N,N-dimethyl-N($C_{8-18}$-coconut acylamidopropyl)amine N-oxide (about 35% active substance content in water; INCI name: Cocamidopropylamine Oxide) (Goldschmidt)

26 poly(dimethyldiallylammonium chloride) (about 40% active substance content; INCI name: Polyquaternium-6) (Ondeo-Nalco)

27 silk protein (INCI name: Silk Serica (Linne)) (Ikeda Bussan Kaisha)

28 1-hydroxyethane-1,1-diphosphonic acid (about 58–61% active substance content in water; INCI name: Etidronic Acid, Aqua (Water)) (Solutia)

29 enzymatically obtained hydrolyzate from virgin Merino wool (about 21–23% active substance content; INCI name: Aqua (Water), Hydrolyzed Keratin, Phenoxyethanol, Methylparaben, Butyl-paraben, Ethylparaben, Propylparaben) (Cognis)

30 4-[(2-hydroxyethyl)amino]-3-nitrophenol (INCI name: 3-Nitro-p-hydroxyethylaminophenol)

31 2-amino-6-chloro-4-nitrophenol 32 lauryl ether sulfate sodium salt (at least 26.5% active substance content; INCI name: Sodium Laureth Sulfate) (Cognis)

33 nonionic silicone emulsion (10% active substance content; INCI name: Dimethicone) (Dow Corning)

34 acrylic polymer (about 28% active substance content; INCI name: Acrylates Copolymer) (Rohm % Haas)

The invention claimed is:

1. A composition for dyeing keratinic fibers, comprising, in a cosmetically acceptable carrier, at least one p-phenylenediamine derivative compound of the formula (I)

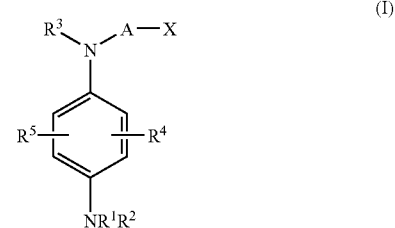

wherein

A is a branched or unbranched alkylene group having 2 to 6 carbon atoms, which can optionally carry one or more substituents, selected from hydroxy group(s) and halogen atom(s), X is an optionally substituted imidazolyl radical, $R^1$, $R^2$ and $R^3$ are, independently of one another, a hydrogen atom, a $C_1$- to $C_4$-alkyl group, a $C_1$- to $C_4$-monohydroxyalkyl group or a $C_2$- to $C_6$-poly-hydroxyalkyl group, and $R^4$ and $R^5$ are, independently of one another, a hydrogen atom, a $C_1$- to $C_4$-alkyl group, a $C_1$- to $C_4$-alkoxy group, a $C_1$- to $C_4$-monohydroxyalkyl group, a $C_2$- to $C_4$-polyhydroxyalkyl group or a halogen atom.

2. The composition of claim 1 wherein A is an ethylene group.

3. The composition of claim 2 wherein the compound of formula (I) is (4-aminophenyl)(2-(imidazol-5-yl)ethyl)amine.

4. The composition of claim 1 wherein $R^1$, $R^2$ and $R^3$ are each a hydrogen atom.

5. The composition of claim 4 wherein $R^4$ and $R^5$ are, independently of one another, a hydrogen atom, a methyl group, a chlorine or a fluorine atom.

6. The composition of claim 5 wherein $R^4$ and $R^5$ are each a hydrogen atom.

7. The composition of claim 1 wherein X is an optionally substituted imidazolyl radical of the formula (II)

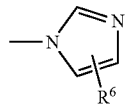
(II)

where R6 is a hydrogen atom, a $C_1$- to $C_4$-alkyl group, a $C_1$- to $C_4$-monohydroxyalkyl group, a $C_2$- to $C_4$-polyhydroxyalkyl group or a halogen atom.

8. The composition of claim 1 wherein A is a trimethylene group.

9. The composition of claim 8 wherein the compound of the formula (I) is selected from the group consisting of (4-aminophenyl)(3-(imidazol-1-yl)propyl)amine and (4-amino-3-methyl-phenyl)(3-(imidazol-1-yl)propyl)amine.

10. The composition of claim 1 wherein X is an optionally substituted imidazolyl radical of the formula (III)

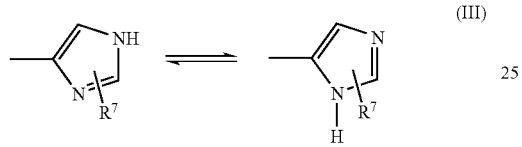
(III)

where R7 is a hydrogen atom, a $C_1$- to $C_4$-alkyl group, a $C_1$- to $C_4$-monohydroxyalkyl group, a $C_2$- to $C_4$-polyhydroxyalkyl group or a halogen atom.

11. A compound having formula (I):

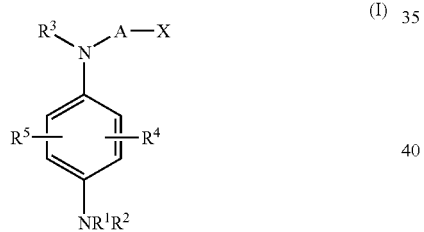
(I)

wherein:
A is an unbranched alkylene group having 2 to 6 carbon atoms;
X is an optionally substituted imidazolyl radical;
$R^1$, $R^2$ and $R^3$ are, independently, H, $C_1$- to $C_4$-alkyl, $C_1$- to $C_4$-monohydroxyalkyl, or $C_2$- to $C_6$-poly-hydroxyalkyl; and
$R^4$ and $R^5$ are, independently, H, $C_1$- to $C_4$-alkyl, $C_1$- to $C_4$-alkoxy, $C_1$- to $C_4$-monohydroxyalkyl, $C_2$- to $C_4$-polyhydroxyalkyl, or halogen.

12. The compound of claim 11, wherein X has formula (II):

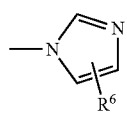
(II)

wherein:
$R^6$ is H, $C_1$ to $C_4$-alkyl, $C_1$- to $C_4$-monohydroxyalkyl, $C_2$- to $C_4$-polyhydroxyalkyl, or halogen.

13. The compound of claim 11, wherein X has formula (III):

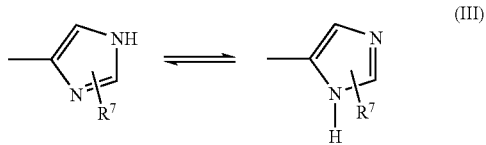
(III)

wherein
$R^7$ is H, $C_1$- to $C_4$-alkyl, $C_1$- to $C_4$-monohydroxyalkyl, $C_2$- to $C_4$-polyhydroxyalkyl, or halogen.

14. The compound of claim 11, wherein the compound is (4-Aminophenyl)(2-(imidazol-5-yl)ethyl)amine.

15. A process for dyeing keratinic fibers comprising applying to the keratin fibers a composition comprising a compound of claim 11, and after a period of time rinsing off the composition from the keratin fibers.

16. A compound having formula (I):

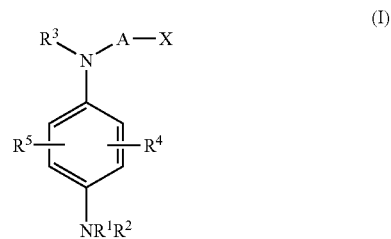
(I)

wherein:
A is an unbranched alkylene group having 1 to 6 carbon atoms;
X is an optionally substituted imidazolyl radical having formula (II):

(II)

$R^1$, $R^2$ and $R^3$ are, independently, H, $C_1$- to $C_4$-alkyl, $C_1$- to $C_4$-monohydroxyalkyl, or $C_2$- to $C_6$-poly-hydroxyalkyl; and
$R^4$ and $R^5$ are, independently, H, $C_1$- to $C_4$-alkyl, $C_1$- to $C_4$-alkoxy, $C_1$- to $C_4$-monohydroxyalkyl, $C_2$- to $C_4$-polyhydroxyalkyl, or halogen; and
$R^6$ is H, $C_1$ to $C_4$-alkyl, $C_1$- to $C_4$-monohydroxyalkyl, $C_2$- to $C_4$-polyhydroxyalkyl, or halogen.

17. The compound of claim 16, wherein A is an unbranched alkylene group having 2 to 6 carbon atoms.

18. The compound of claim 16, wherein A is trimethylene.

19. The compound of claim 16, wherein the compound is (4-amino-phenyl)(3-(imidazol-1-yl)propyl)amine or (4-amino-3-methylphenyl)(3-(imidazol-1-yl)propyl)amine.

20. A composition for dyeing keratinic fibers, comprising:
a cosmetically acceptable carrier, and
a compound of claim 16.

21. A process for dyeing keratinic fibers, comprising:
applying a composition comprising a compound of claim 16 to the keratin fibers and then rinsing the composition from the keratin fibers.

* * * * *